(12) United States Patent
Le

(10) Patent No.: US 11,009,775 B2
(45) Date of Patent: *May 18, 2021

(54) ORAL PHOTOGRAPHY SYSTEM

(71) Applicant: Vu Quang Le, Trabuco, CA (US)

(72) Inventor: Vu Quang Le, Trabuco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,580

(22) Filed: Apr. 20, 2020

(65) Prior Publication Data

US 2020/0301251 A1 Sep. 24, 2020

Related U.S. Application Data

(63) Continuation-in-part of application No. 16/358,147, filed on Mar. 19, 2019, now Pat. No. 10,667,696.

(51) Int. Cl.
*G03B 15/06* (2021.01)
*A61B 1/24* (2006.01)
*A61B 1/00* (2006.01)

(52) U.S. Cl.
CPC ............ *G03B 15/06* (2013.01); *A61B 1/0011* (2013.01); *A61B 1/00128* (2013.01); *A61B 1/00147* (2013.01); *A61B 1/24* (2013.01); *A61B 2562/12* (2013.01)

(58) Field of Classification Search
None
See application file for complete search history.

(56) References Cited

U.S. PATENT DOCUMENTS

| | | | |
|---|---|---|---|
| 2,560,884 A * | 7/1951 | Nagourney | A61B 5/0077 248/124.1 |
| 3,374,342 A * | 3/1968 | Hutchins | G03B 15/03 362/8 |
| 4,392,183 A * | 7/1983 | Ostlund | G03B 15/03 362/11 |
| 7,050,715 B1 * | 5/2006 | Carrington | G03B 15/035 396/182 |
| 10,667,696 B1 * | 6/2020 | Le | G03B 17/561 |
| 2016/0202598 A1 * | 7/2016 | Griffey | H04N 5/23206 396/58 |
| 2016/0277660 A1 * | 9/2016 | Kaiser | F16B 2/12 |
| 2017/0118385 A1 * | 4/2017 | Vargas | G02B 7/1824 |
| 2020/0301251 A1 * | 9/2020 | Le | A61B 1/0011 |

OTHER PUBLICATIONS

Smile Line, Smile Line MDP KIT—#6600-KIT, Mar. 19, 2019, https://smilelineusa.com/product/smile-lite-mdp-full-set-6600-kit/.
Photomed, SDL—Smartphone Dental Light, Mar. 19, 2019, https://www.photomed.net/sdl.htm.

\* cited by examiner

*Primary Examiner* — William B Perkey
(74) *Attorney, Agent, or Firm* — John D. Tran; Rhema Law Group

(57) ABSTRACT

An oral photography system and method can include: a chassis, the chassis including a chassis base and a vertical chassis extension, the vertical chassis extension extending upward from the chassis base, and the vertical chassis extension including: a magnetic clamp having a first clamping element for securing an imaging device to the vertical chassis extension, the imaging device including a second clamping element, a diffusion panel attachment coupled to the vertical chassis extension, and a light panel attachment coupled to the vertical chassis extension; a diffusion panel releasably affixed to the diffusion panel attachment; and a light panel releasably affixed to the light panel attachment.

20 Claims, 14 Drawing Sheets

ORAL PHOTOGRAPHY SYSTEM

CROSS-REFERENCE TO RELATED APPLICATIONS

This is a Continuation-In-Part of U.S. patent application Ser. No. 16/358,147 filed Mar. 19, 2019 and claims priority benefit to all common subject matter. The content of this applications is incorporated herein by reference.

TECHNICAL FIELD

This disclosure relates to photography, more particularly to a system for oral photography.

BACKGROUND

Photographic and video records for use in medical and dental procedures is becoming more important as the ability to capture, store, and analyze these records increases. The single lens reflex camera produces good images but, due to many problems, has failed to provide a useable solution suitable for broad application within the health care industry.

One problem with the single lens reflex camera is the weight. The heft of the camera itself can make it difficult for smaller professionals to maneuver the camera in place and, once there, to maintain stability.

Another problem with the single lens reflex camera is the width of the camera and lens. The width of the camera can make precise angles and tight quarters a challenge.

The size and weight of the single lens reflex camera are only compounded when the camera is used in conjunction with a lighting apparatus. Some lighting apparatuses use a removable diffuser that is either flush with the front surface, resulting in minimal diffusion of light, or a magnetic mount offset diffuser which falls off in real life use.

With the rise in the use and reliance on video in the medicine and dentistry, it is critical that solutions be found to these problems. Solutions have been long sought but prior developments have not taught or suggested any complete solutions, and solutions to these problems have long eluded those skilled in the art. Thus, there remains a considerable need for devices and methods that can reduce weight and width of a photography system for allowing broad application within the health care field.

SUMMARY

An oral photography system and methods, providing significantly reduced weight and width for allowing broad application within the health care field, are disclosed. The oral photography system and methods can include: a chassis, the chassis including a chassis base and a vertical chassis extension, the vertical chassis extension extending upward from the chassis base, and the vertical chassis extension including: a magnetic clamp having a first clamping element for securing an imaging device to the vertical chassis extension, the imaging device including a second clamping element, a diffusion panel attachment coupled to the vertical chassis extension, and a light panel attachment coupled to the vertical chassis extension; a diffusion panel releasably affixed to the diffusion panel attachment; and a light panel releasably affixed to the light panel attachment.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The photography system is illustrated in the figures of the accompanying drawings which are meant to be exemplary and not limiting, in which like reference numerals are intended to refer to like components, and in which.

DETAILED DESCRIPTION

Figure 1:
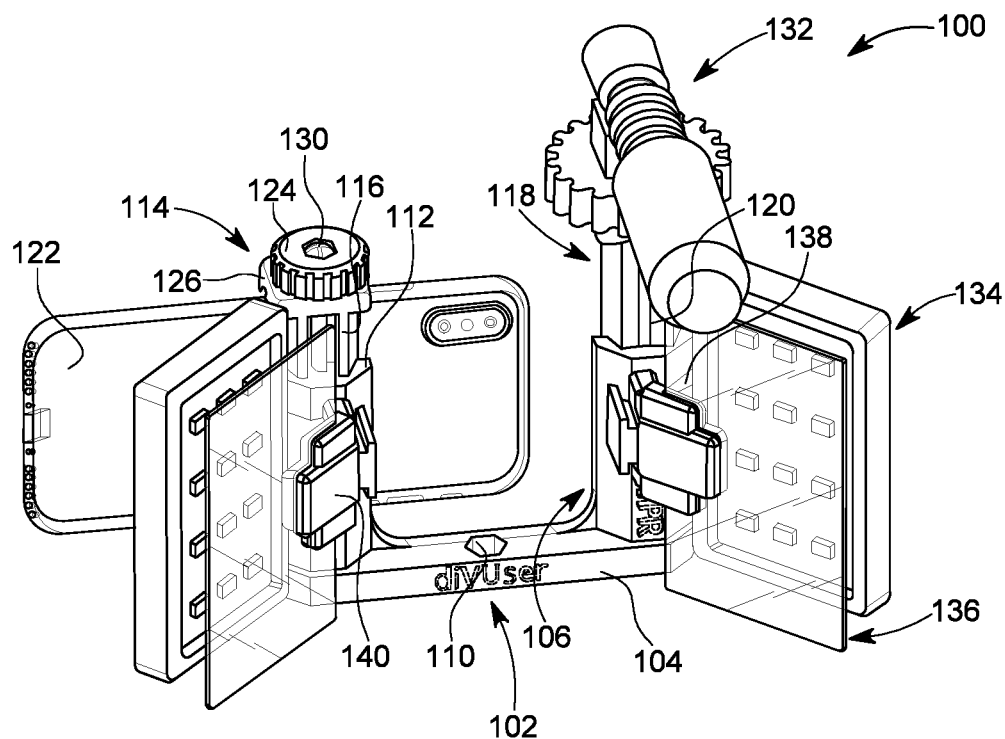
FIG. 1 is a front isometric view of the photography system in a first embodiment.

In the following description, reference is made to the accompanying drawings that form a part hereof, and in which are shown by way of illustration, embodiments in which the photography system may be practiced. It is to be understood that other embodiments may be utilized and structural changes may be made without departing from the scope of the photography system.

When features, aspects, or embodiments of the photography system are described in terms of steps of a process, an operation, a control flow, or a flow chart, it is to be understood that the steps can be combined, performed in a different order, deleted, or include additional steps without departing from the photography system as described herein.

The photography system is described in sufficient detail to enable those skilled in the art to make and use the photography system and provide numerous specific details to give a thorough understanding of the photography system; however, it will be apparent that the photography system may be practiced without these specific details.

In order to avoid obscuring the photography system, some well-known system configurations and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGs. Generally, the photography system can be operated in any orientation.

As used herein, the term system is defined as a device or method depending on the context in which it is used. For expository purposes, the term "horizontal" as used herein is defined as a plane parallel to the bottom plane or surface of the chassis base, regardless of its orientation. The term "vertical" refers to a direction perpendicular to the horizontal as just defined. Terms, such as "above", "below", "bottom", "top", "side", "higher", "lower", "upper", "over", and "under", are defined with respect to the horizontal plane. The term "couple" as in coupling or coupled means physical contact between elements whether direct or indirect.

Referring now to FIG. 1, therein is shown a front isometric view of the photography system 100 in a first embodiment. The photography system 100 is shown having a chassis 102.

The chassis 102 can include a chassis base 104 spanning horizontally between two vertical chassis extensions 106.

The chassis base 104 can include a frame mount 110. The frame mount 110 can be a mount configured for compatibility with a tripod, monopod, or gimbal for more stable video quality. It is further contemplated that some users may optionally mount a pistol grip to the frame mount 110.

The vertical chassis extensions 106 can extend upward from the chassis base 104. The vertical chassis extensions 106 can include chassis rails 112. The chassis rails 112 can enable the chassis 102 to be connected to device clamps 114 through the mating of device clamp rails 116 with the chassis rails 112.

The chassis rails 112 can further enable the chassis 102 to be connected to external mounts 118 through the mating of external mount rails 120 and the chassis rails 112. It is contemplated that the device clamps 114 and the external mounts 118 can be moveably coupled to the chassis 102.

The device clamps 114 can be adjusted vertically with respect to the chassis 102. The device clamp rails 116, being male, can be mated with the female chassis rails 112 for providing adjustable clamping for an imaging device 122.

The imaging device 122 can be a smart phone of various available widths and thicknesses. The device clamps 114 can include a tightening extension 124 coupled to a top clasp 126, a bottom clasp (shown in FIG. 2), and a screw 130.

The tightening extension 124 can be a thumbwheel or a set of tightening wheels used to tighten the device clamps 114 onto the imaging device 122. The tightening extension 124 is shown extended above the imaging device 122 for top access and ease of use. The top clasp 126 and the bottom clasp can both have the device clamp rails 116 formed thereon and can thereby mate with the chassis rails 112 for vertical movement.

The screw 130 can extend through the tightening extension 124, the top clasp 126, and the bottom clasp. Tightening the screw 130 by twisting the tightening extension 124 can force the top clasp 126 toward the bottom clasp to secure the imaging device 122.

Alternatively, it is contemplated that the screw 130 can be tightened into the chassis 102 by twisting the tightening extension 124. Tightening the screw 130 would also bring the top clasp 126 toward the bottom clasp as well as the chassis base 104 to secure the imaging device 122.

It is contemplated that the screw 130 may be left loose by a few millimeters. The tightening extension 124 can still be used to tighten the top clasp 126 as long as the screw 130 is engaged into the chassis 102. The tightening extension 124 may be loosened quickly yet, the head of the screw 130 can be retained within the tightening extension 124 without falling out.

In this way the head of the screw 130 can become a preset point from which to begin retightening the tightening extension 124. A properly set screw 130 would allow very fast removal and reattachment of the screw 130, because the minimum travel of the tightening extension 124 to allow imaging device 122 removal would be stored in the position of the screw 130.

The external mounts 118 can allow users to attach an external equipment 132. Illustratively, for example, the external mounts 118 can allow a user to mount an external microphone to be used with the imaging device 122 as is shown.

It is alternatively contemplated that the external mounts 118 can be used to secure larger, more powerful LED panels to the chassis 102. It is contemplated that the external mounts 118 can implement a hot shoe mount, which can allow mounting of many various external equipment. The tightening extension 124 can be located above the imaging device 122 and can be tightened down onto the imaging device 122.

The imaging device 122 can be positioned and affixed using the device clamps 114. The camera of the imaging device 122 can be positioned between the vertical chassis extensions 106 and can acquire images through the vertical chassis extensions 106.

To each of the vertical chassis extensions 106, light panels 134 and diffusion panels 136 can be mounted. As is shown, one of the light panels 134 and one of the diffusion panels 136 are affixed to each of the vertical chassis extensions 106.

The light panels 134 can be affixed to the vertical chassis extensions 106 with light panel attachments 138 while the diffusion panels 136 can be affixed to the vertical chassis extensions 106 with diffusion panel attachments 140. The light panels 134 can be battery powered LED panels used for illumination of dental and closeup photographs.

The light panels 134 can be rotationally oriented at 180 degrees from each other so their power switches (not pictured) are both on a single side such as on a top side. The diffusion panels 136 can be a translucent white acrylic diffusion panel for example.

It has been discovered that implementing the photography system 100 as described can provide cross lighting to teeth with a heavily diffused light. As will be appreciated this gives a glossy, yet textured look to the enamel.

That is, the light panels 134, the diffusion panels 136 and the imaging device 122 coupled together as shown and described can light teeth bilaterally with significant diffusion of the light. This creates uniform, soft lighting approximating the appearance of much larger, much more expensive studio lighting.

Figure 2:
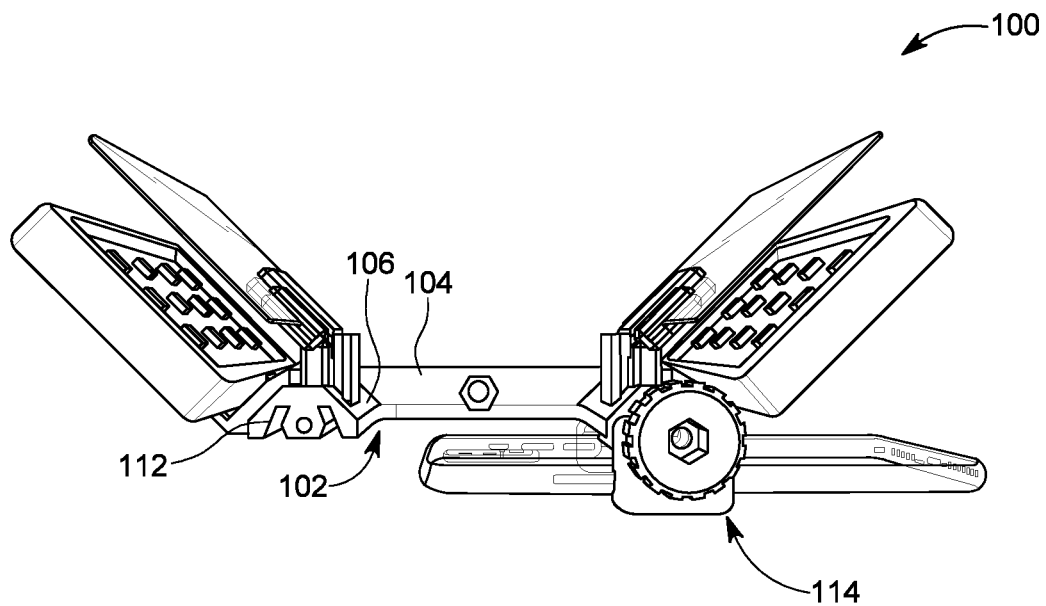
FIG. 2 is a top isometric view of the photography system of FIG. 1.

Referring now to FIG. 2, therein is shown a top isometric view of the photography system 100 of FIG. 1. The photography system 100 is shown with the chassis 102 with the vertical chassis extensions 106 extending up away from the chassis base 104.

The chassis rails 112 are depicted and shown formed within one of the vertical chassis extensions 106. It will be appreciated that the vertical chassis extensions 106 having the device clamps 114 also includes the chassis rails 112 mated to the device clamp rails 116 of FIG. 1 for the device clamps 114.

Figure 3:
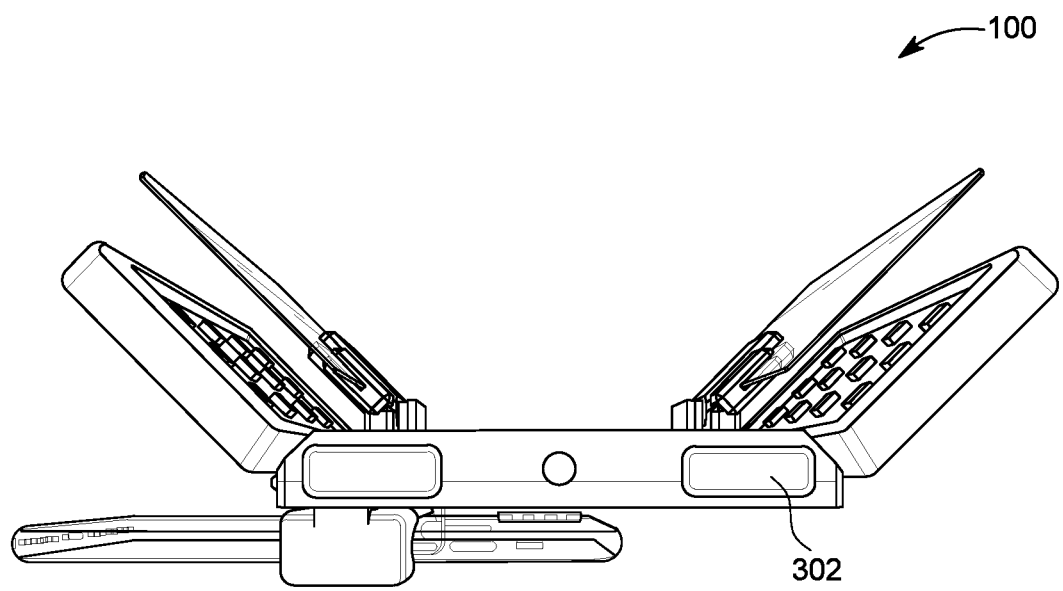
FIG. 3 is a bottom isometric view of the photography system of FIG. 1.

Referring now to FIG. 3, therein is shown a bottom isometric view of the photography system 100 of FIG. 1. The photography system 100 is shown having depressions 302. The depressions 302 can provide a thumb rest for the user to increase both comfort and to provide a more secure purchase on the photography system 100.

Figure 4:
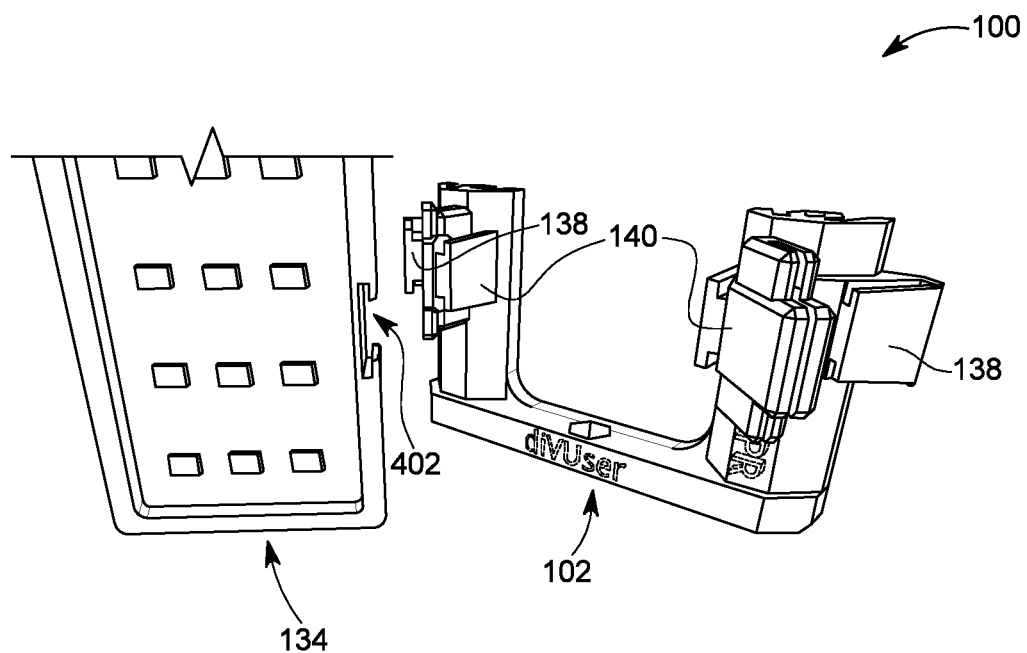
FIG. 4 is a front isometric view of the photography system of FIG. 1 in an attachment phase of operation.

Referring now to FIG. 4, therein is shown a front isometric view of the photography system 100 of FIG. 1 in an attachment phase of operation. The photography system 100 is shown having the chassis 102 adjacent to the light panels 134.

The chassis 102 is shown having the light panel attachments 138 along with the diffusion panel attachments 140. The light panel attachments 138 can be a tapered plane of plastic providing a friction fit between the light panel attachments 138 and a receiving recess 402 within the light panels 134.

The light panel attachments 138 can retain the light panels 134 to the chassis 102. The light panel attachments 138 can be a friction fit wedge and can be pushed into the receiving recess 402 of the light panels 134, the light panels 134 are tightened against the widening taper of the light panel attachments 138.

Again, the light panel attachments 138 is shown to gradually widen towards its posterior, providing a tighter fit as the light panels 134 are pressed onto the light panel attachments 138. It is contemplated that the light panel attachments 138 is over widened to allow for more retention as the plastic wears over time.

The diffusion panel attachments 140 can also be seen as a friction fit clamp for holding the diffusion panels 136 of FIG. 1. As the diffusion panels 136 are pushed into the diffusion panel attachments 140 the diffusion panels 136 are held ever more securely.

Figure 5:
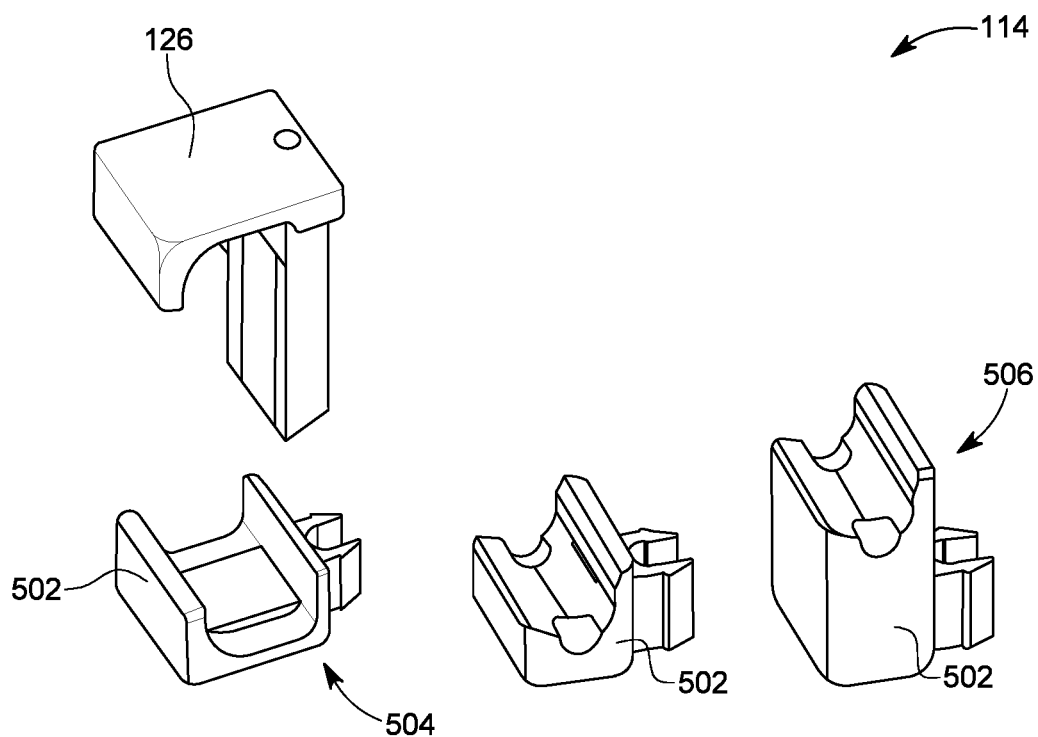
FIG. 5 is an isometric view of the device clamps of FIG. 1.

Referring now to FIG. 5, therein is shown an isometric view of the device clamps 114 of FIG. 1. Portions of the device clamps 114 are shown, specifically the top clasp 126 and bottom clasps 502 are shown.

As will be appreciated, the top clasp 126 and the bottom clasp 502 are shown with a widened cross section 504 to support larger imaging devices 122 of FIG. 1 or imaging devices 122 having extended battery attachments.

The top clasp 126 and the bottom clasp 502 can also have a thicker cross section 506 to support narrow or slim imaging devices 122. It is alternatively contemplated that when the imaging device 122 is used on the opposite side, or left side, of the chassis 102 of FIG. 1 the bottom clasp 502 having the thicker cross section 506 can be used to lift the camera lens upward, above the chassis base 104 of FIG. 1 when clamped down.

The bottom clasps 502 and the top clasps 126 are shown having cutouts 508. The cutouts 508 can prevent the buttons on the imaging device 122 from being depressed when the imaging device 122 is clamped down. This allows more latitude in imaging device 122. It is contemplated that the various structural layouts of the top clasp 126 and the bottom clasp 502 will accommodate all major imaging devices 122, even if they have thick cases.

The bottom clasps 502 are depicted having mounting clips 510. The mounting clips 510 can have a hollow center for allowing the screw 130 of FIG. 1 to pass therethrough.

Figure 6:
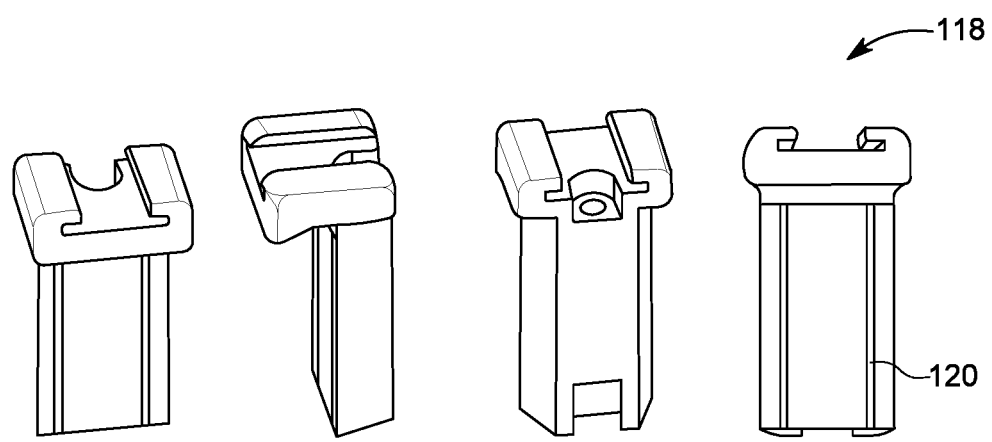
FIG. 6 is an isometric view of the external mounts of FIG. 1.

Referring now to FIG. 6, therein is shown an isometric view of the external mounts 118 of FIG. 1. The external mounts 118 are shown having the external mount rails 120 formed therein.

The external mounts 118 can be configured with a hot shoe attachment. The hot shoe attachment is compatible with a wide variety of videography and photography accessories, such as external microphones, lighting devices, flashes, and others.

Figure 7:
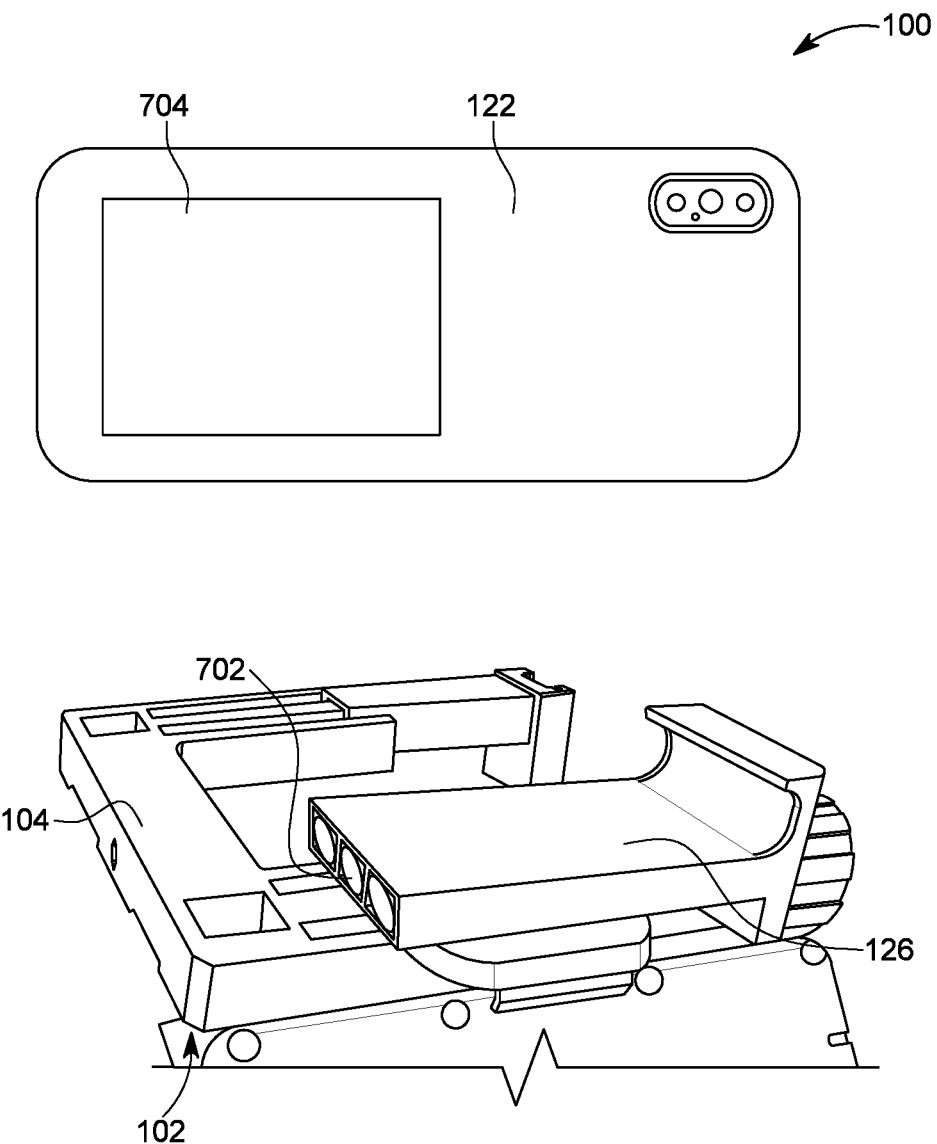
FIG. 7 is a back isometric view of the photography system of FIG. 1.

Referring now to FIG. 7, therein is shown a back isometric view of the photography system 100 of FIG. 1. The photography system 100 is shown with the top clasp 126 having magnets 702.

The magnets 702 are depicted on the top clasp 126 near the chassis base 104. It is contemplated that each of the top clasps 126 can include the magnets 702 whether exposed from a side of the top clasp 126, as shown in FIG. 7, or fully enclosed within the top clasps 126.

The magnets 702 can be aligned with a magnetic adhesive 704 adhered to the imaging device 122. The magnetic adhesive 704 can be a metallic or magnetic disc or adhesive that can be installed on the imaging device 122.

It has been discovered that the inclusion of the magnets 702 together with the magnetic adhesive 704 can rigidly hold the imaging device 122 to the top clasp 126. Further, the magnetic adhesive 704 together with the magnets 702 can enable immediate alignment between the imaging device 122 and the chassis 102.

Figure 8:
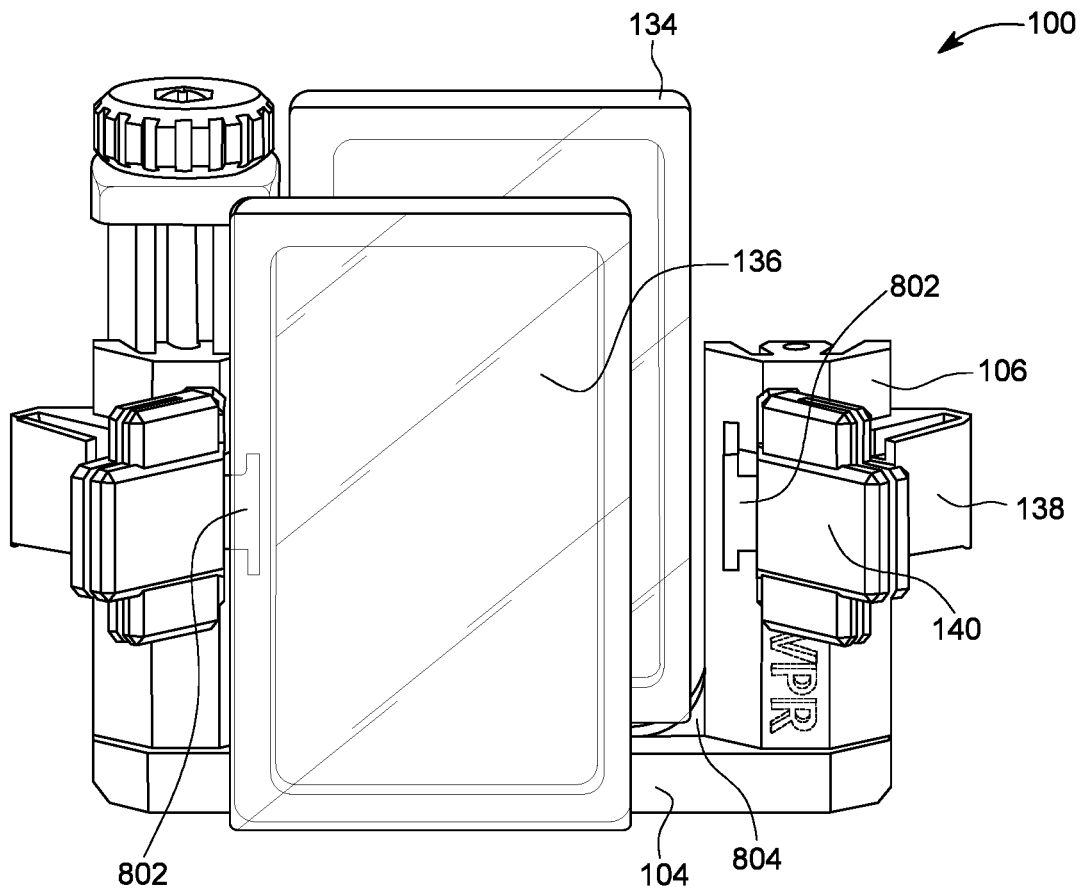
FIG. 8 is a front isometric view of the photography system of FIG. 1 in a closed configuration.

Referring now to FIG. 8, therein is shown a front isometric view of the photography system 100 of FIG. 1 in a closed configuration. The light panels 134 and the diffusion panels 136 can be stored and positioned on the chassis base 104 between the vertical chassis extensions 106.

The light panel 134 and the diffusion panel 136 between the vertical chassis extensions 106 can be detached from the light panel attachments 138 and the diffusion panel attachments 140, respectively.

One of the light panels 134 can be attached to storage attachments 802 on both of the vertical chassis extensions 106. The storage attachments 802 can be similar in form and function to the light panel attachments 138 of FIG. 1 described above.

However, the position of the storage attachments 802 enables one of the light panels 134 and the diffusion panels 136 to be stored and secured between the vertical chassis extensions 106 and the other of the two light panels 134, which is coupled to the storage attachments 802. The light panel 134 and the diffusion panels 136 can rest on the vertical chassis extensions 106 and a storage back 804.

Figure 9:
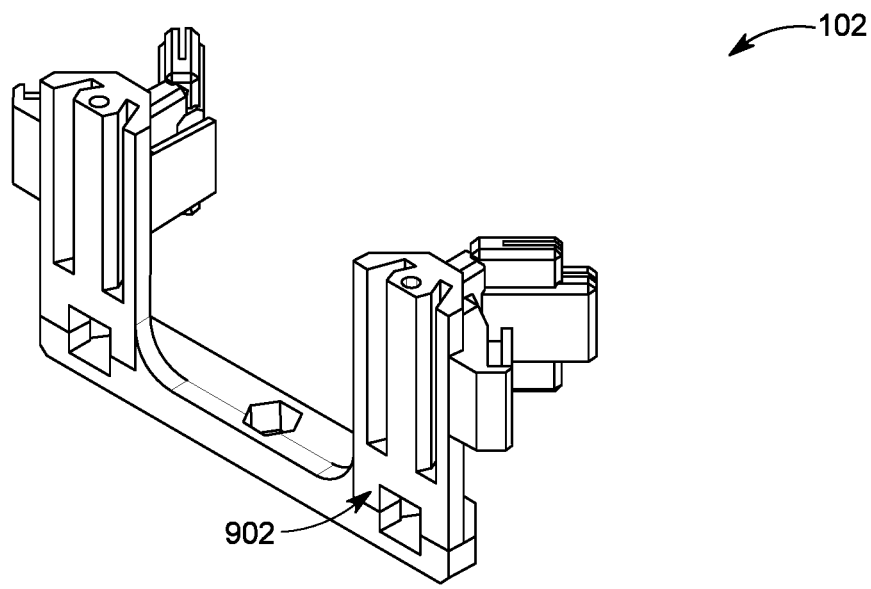
FIG. 9 is a back isometric view of the chassis of FIG. 1.

Referring now to FIG. 9, therein is shown a back isometric view of the chassis 102 of FIG. 1. The chassis 102 is shown to be symmetrical about a vertical axis. This can allow the imaging device 122 of FIG. 1 to be used on either the left or right side. Similarly, the external mounts 118 of FIG. 1 can be used and mounted on either the right or left side.

The chassis 102 is shown having mounting recesses 902 for receiving the mounting clips 510 of FIG. 5 of the bottom clasps 502 of FIG. 5. When configured to use the mounting recesses 902 with the mounting clips 510, the bottom clasps 502 will be stationary with respect to the chassis 102 unlike the top clasp 126 of FIG. 1 which would be vertically moveable.

Figure 10:
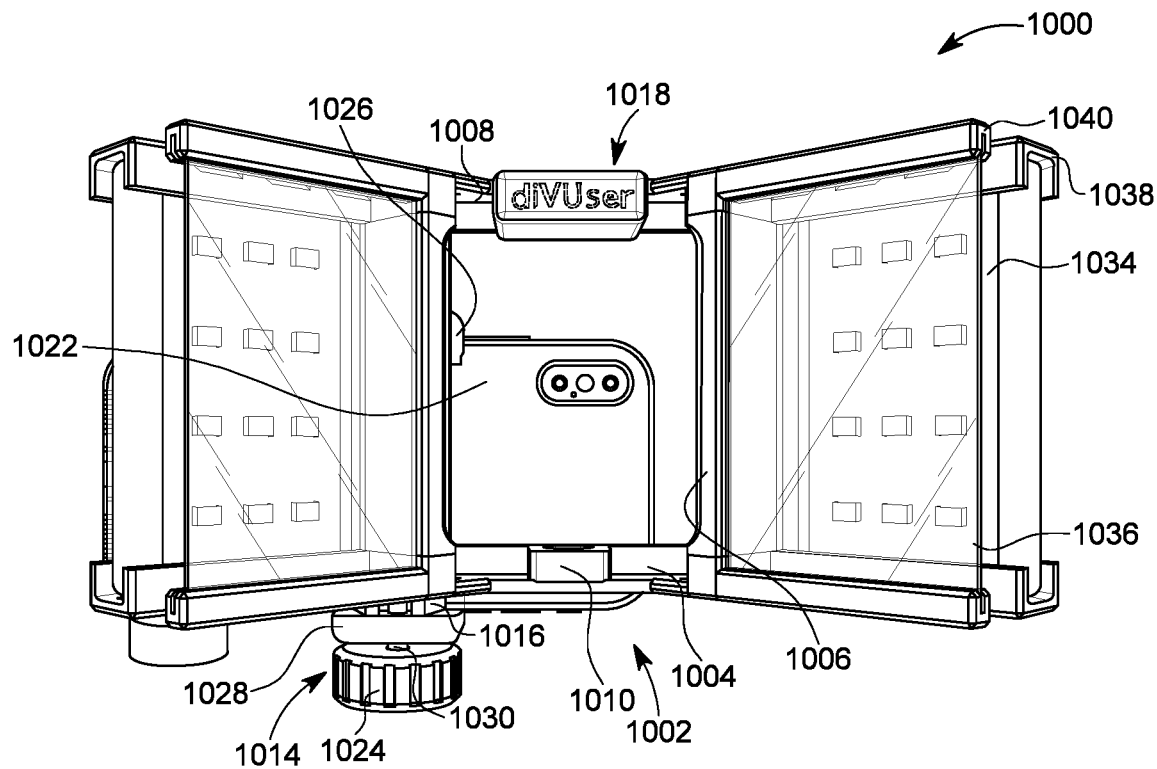
FIG. 10 is a front isometric view of the photography system in a second embodiment.

Referring now to FIG. 10, therein is shown a front isometric view of the photography system 1000 in a second embodiment. The photography system 1000 is shown having a chassis 1002.

The chassis 1002 can include a chassis base 1004 spanning horizontally between two vertical chassis extensions 1006.

The chassis base 1004 can include a frame mount 1010. The frame mount 1010 can be a mount configured for compatibility with a tripod, monopod, or gimbal for more stable video quality. It is further contemplated that some users may optionally mount a pistol grip to the frame mount 1010.

The vertical chassis extensions 1006 can extend upward from the chassis base 1004 to a chassis top 1008. The vertical chassis extensions 1006 can include chassis rails similar to the chassis rails 112 of FIG. 1. The chassis rails can enable the chassis 1002 to be connected to device clamps 1014 through the mating of device clamp rails 1016 with the chassis rails. It is contemplated that the device clamps 1014 can be moveably coupled to the chassis 1002.

The vertical chassis extensions 1006 can further enable the chassis 1002 to be connected to and incorporate external mounts 1018. The external mounts 1018 can be seen spanning between the vertical chassis extensions 1006.

The device clamps 1014 can be adjusted vertically with respect to the chassis 1002. The device clamp rails 1016, being male, can be mated with the female chassis rails for providing adjustable clamping for an imaging device 1022.

The imaging device 1022 can be a smart phone of various available widths and thicknesses. The device clamps 1014 can include a tightening extension 1024 coupled to a top clasp 1026, a bottom clasp 1028, and a screw 1030.

The tightening extension 1024 can be a thumbwheel or a set of tightening wheels used to tighten the device clamps 1014 onto the imaging device 1022. The tightening extension 1024 is shown extended below the imaging device 122 for bottom access and ease of use. The top clasp 1026 and the bottom clasp 1028 can both have the device clamp rails 1016 formed thereon and can thereby mate with the chassis rails for vertical movement.

The screw 1030 can extend through the tightening extension 1024, the top clasp 1026, and the bottom clasp 1028. Tightening the screw 1030 by twisting the tightening extension 1024 can force the top clasp 1026 toward the bottom clasp to secure the imaging device 1022.

Alternatively, it is contemplated that the screw 1030 can be tightened into the chassis 1002 by twisting the tightening extension 1024. Tightening the screw 1030 would also bring the top clasp 1026 toward the bottom clasp as well as the chassis base 1004 to secure the imaging device 1022.

It is contemplated that the screw 1030 may be left loose by a few millimeters. The tightening extension 1024 can still be used to tighten the top clasp 1026 as long as the screw 1030 is engaged into the chassis 1002. The tightening extension 1024 may be loosened quickly yet, the head of the screw 1030 can be retained within the tightening extension 1024 without falling out.

In this way the head of the screw 1030 can become a preset point from which to begin retightening the tightening extension 1024. A properly set screw 1030 would allow very fast removal and reattachment of the screw 1030, because the minimum travel of the tightening extension 1024 to allow imaging device 1022 removal would be stored in the position of the screw 1030.

The external mounts 1018 can allow users to attach an external equipment. Illustratively, for example, the external mounts 1018 can allow a user to mount an external microphone to be used with the imaging device 1022.

It is alternatively contemplated that the external mounts 1018 can be used to secure larger, more powerful LED panels to the chassis 1002. It is contemplated that the external mounts 1018 can implement a hot shoe mount, which can allow mounting of many various external equipment. The tightening extension 1024 can be located above the imaging device 1022 and can be tightened down onto the imaging device 1022.

The imaging device 1022 can be positioned and affixed using the device clamps 1014. The camera of the imaging device 1022 can be positioned between the vertical chassis extensions 1006 and can acquire images through the vertical chassis extensions 1006.

To each of the vertical chassis extensions 1006, light panels 1034 and diffusion panels 1036 can be mounted. As is shown, one of the light panels 1034 and one of the diffusion panels 1036 are affixed to each of the vertical chassis extensions 1006.

The light panels 1034 can be affixed to the vertical chassis extensions 1006 with light panel attachments 1038 while the diffusion panels 1036 can be affixed to the vertical chassis extensions 1006 with diffusion panel attachments 1040. The light panel attachments 1038 can be a slot providing a friction fit.

That is the light panels 1034 can be slid into a slightly tapered slot, which comprises the light panel attachments 1038. The light panels 1034 are then held securely within the light panel attachments 1038 allowing the photography system 1000 to be manipulated without risk of the light panels 1034 becoming detached from the chassis 1002.

The light panels 1034 can be battery powered LED panels used for illumination of dental and closeup photographs. The light panels 1034 can be rotationally oriented at 180 degrees from each other so their power switches (not pictured) are both on a single side such as on a top side.

The diffusion panels 1036 can be a translucent white acrylic diffusion panel for example. The diffusion panel attachments 1040 can be a slot providing a friction fit.

That is the diffusion panels 1036 can be slid into a slightly tapered slot, which comprises the diffusion panel attachments 1040. The diffusion panels 1036 are then held securely within the diffusion panel attachments 1040 allowing the photography system 1000 to be manipulated without risk of the diffusion panels 1036 becoming detached from the chassis 1002.

It has been discovered that implementing the photography system 1000 as described can provide cross lighting to teeth with a heavily diffused light. As will be appreciated this gives a glossy, yet textured look to the enamel.

That is, the light panels 1034, the diffusion panels 1036 and the imaging device 1022 coupled together as shown and described can light teeth bilaterally with significant diffusion of the light. This creates uniform, soft lighting approximating the appearance of much larger, much more expensive studio lighting.

The diffusion panel attachments 1040 together with the light panel attachments 1038 can have a fixed mounting position with respect to the imaging device 1022 and with respect to the chassis 1002. The fixed mounting position creates consistently soft light, which improves the highlights on the teeth, and significantly minimizes eye strain to the patient.

The fixed mounting of the light panels 1034 can have a fixed angle of 45 degrees off the chassis 1002, or 135 degrees spanning between the light panels 1034. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 11:
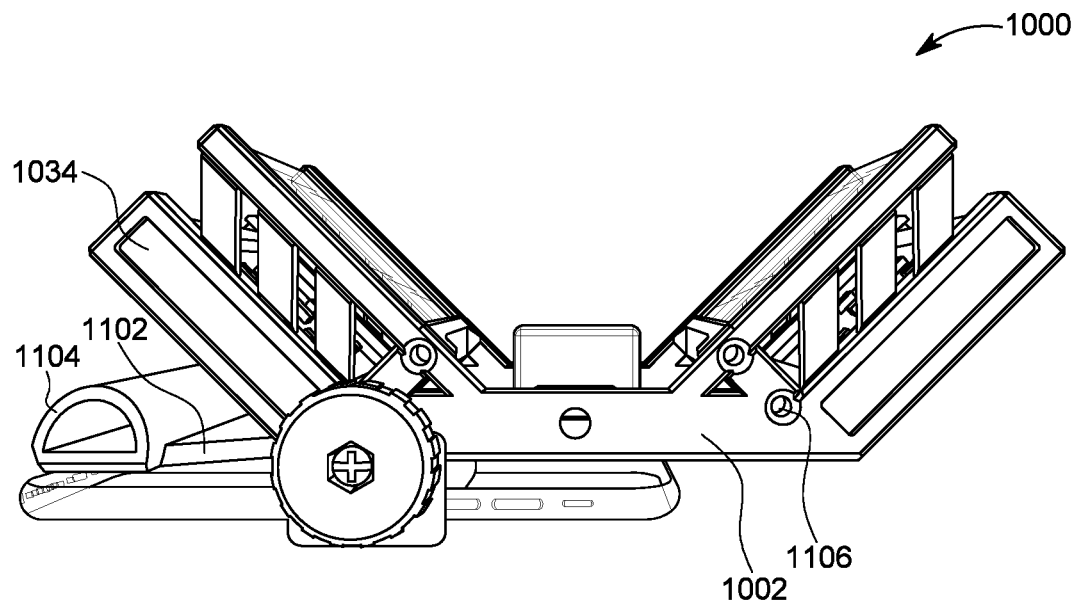
FIG. 11 is a bottom isometric view of the photography system of FIG. 10.

Referring now to FIG. 11, therein is shown a bottom isometric view of the photography system 1000 of FIG. 10. The photography system 1000 is shown having a grip bar 1102 with a handle 1104.

The grip bar 1102 can allow a user to operate the photography system 1000 with a single hand, with fingers sandwiched between the grip 1104 and the bottom surface of the right light panel 1034. A cutout 1106 in the chassis 1002 can allow a charging cable for the light panels 1034 to passthrough. This can enable the light panels 1034 to be charged without removing the light panels 1034 from the chassis 1002.

Figure 12:
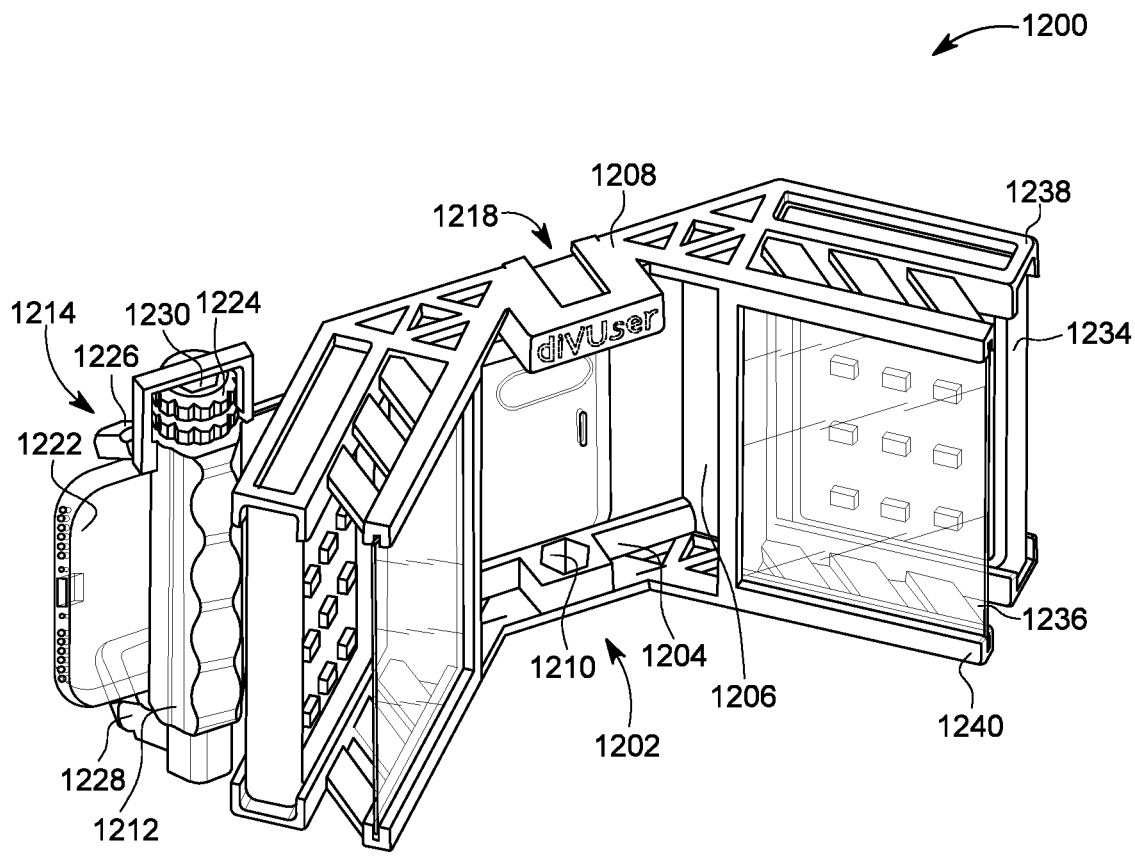
FIG. 12 is a top front isometric view of the photography system in a third embodiment.

Referring now to FIG. 12, therein is shown a top front isometric view of the photography system 1200 in a third embodiment. The photography system 1200 is shown having a chassis 1202.

The chassis 1202 can include a chassis base 1204 spanning horizontally between two vertical chassis extensions 1206.

The chassis base 1204 can include a frame mount 1210. The frame mount 1210 can be a mount configured for compatibility with a tripod, monopod, or gimbal for more stable video quality. It is further contemplated that some users may optionally mount a pistol grip to the frame mount 1210.

The vertical chassis extensions 1206 can extend upward from the chassis base 1204 to a chassis top 1208. The vertical chassis extensions 1206 can include chassis rails similar to the chassis rails 112 of FIG. 1 within a handle 1212 extended horizontally away from one of the vertical chassis extensions 1206.

As is illustratively depicted, the outer surface of the vise clamp also doubles the handle 1212 to hold the photography system 1200 like a traditional camera. When using this grasp, the shutter buttons on most phone apps are accessible with the user's right thumb. This has been discovered to provide intuitive and effective one handed operation. It will be appreciated that the photography system 1200 can allow a user to operate the smartphone with the right hand, while positioning a mirror or retractor with the other hand. The entire rig may be inverted to use with the left hand. It is contemplated that all current smartphones will orient their apps and their images to compensate.

The chassis rails can enable the chassis 1202 to be connected to device clamps 1214 through the mating of device clamp rails, similar to the device clamp rails 116 of FIG. 1, with the chassis rails. It is contemplated that the device clamps 1214 can be moveably coupled to the chassis 1202.

The vertical chassis extensions 1206 can further enable the chassis 1202 to be connected to and incorporate external mounts 1218. The external mounts 1218 can be seen spanning between the vertical chassis extensions 1206.

The device clamps 1214 can be adjusted vertically with respect to the chassis 1202. The device clamp rails can be male and can be mated with the female chassis rails for providing adjustable clamping for an imaging device 1222.

The imaging device 1222 can be a smart phone of various available widths and thicknesses. The device clamps 1214 can include a tightening extension 1224 coupled to a top clasp 1226, a bottom clasp 1228, and a screw 1230.

The tightening extension 1224 can be a thumbwheel or a set of tightening wheels used to tighten the device clamps 1214 onto the imaging device 1222. The tightening extension 1224 is shown extended above the imaging device 1222 for top access and ease of use. The top clasp 1226 and the bottom clasp 1228 can both have the device clamp rails formed thereon and can thereby mate with the chassis rails for vertical movement.

The screw 1230 can extend through the tightening extension 1224, the top clasp 1226, and the bottom clasp 1228. Tightening the screw 1230 by twisting the tightening extension 1224 can force the top clasp 1226 toward the bottom clasp to secure the imaging device 1222. When multiple tightening wheels are used, the tightening wheels can lock the imaging device 1222.

Alternatively, it is contemplated that the screw 1230 can be tightened into the chassis 1202 by twisting the tightening extension 1224. Tightening the screw 1230 would also bring the top clasp 1226 toward the bottom clasp as well as the chassis base 1204 to secure the imaging device 1222.

It is contemplated that the screw 1230 may be left loose by a few millimeters. The tightening extension 1224 can still be used to tighten the top clasp 1226 as long as the screw 1230 is engaged into the chassis 1202. The tightening extension 1224 may be loosened quickly yet, the head of the screw 1230 can be retained within the tightening extension 1224 without falling out.

In this way the head of the screw 1230 can become a preset point from which to begin retightening the tightening extension 1224. A properly set screw 1230 would allow very fast removal and reattachment of the screw 1230, because the minimum travel of the tightening extension 1224 to allow imaging device 1222 removal would be stored in the position of the screw 1230.

The external mounts 1218 can allow users to attach an external equipment. Illustratively, for example, the external mounts 1218 can allow a user to mount an external microphone to be used with the imaging device 1222.

It is alternatively contemplated that the external mounts 1218 can be used to secure larger, more powerful LED panels to the chassis 1202. It is contemplated that the external mounts 1218 can implement a hot shoe mount, which can allow mounting of many various external equipment. The tightening extension 1224 can be located above the imaging device 1222 and can be tightened down onto the imaging device 1222.

The imaging device 1222 can be positioned and affixed using the device clamps 1214. The camera of the imaging device 1222 can be positioned between the vertical chassis extensions 1206 and can acquire images through the vertical chassis extensions 1206.

To each of the vertical chassis extensions 1206, light panels 1234 and diffusion panels 1236 can be mounted. As is shown, one of the light panels 1234 and one of the diffusion panels 1236 are affixed to each of the vertical chassis extensions 1206.

The light panels 1234 can be affixed to the vertical chassis extensions 1206 with light panel attachments 1238 while the diffusion panels 1236 can be affixed to the vertical chassis extensions 1206 with diffusion panel attachments 1240. The light panel attachments 1238 can be a slot providing a friction fit.

That is the light panels 1234 can be slid into a slightly tapered slot, which comprises the light panel attachments 1238. The light panels 1234 are then held securely within the light panel attachments 1238 allowing the photography system 1200 to be manipulated without risk of the light panels 1234 becoming detached from the chassis 1202.

The light panels 1234 can be battery powered LED panels used for illumination of dental and closeup photographs. The light panels 1234 can be rotationally oriented at 180 degrees from each other so their power switches (not pictured) are both on a single side such as on a top side. Further, as is shown, cutouts and holes in the chassis 1202 can allow a USB cable of the light panels 1234 to passthrough. This allows charging of the light panels 1234 without removing it from the chassis.

The diffusion panels 1236 can be a translucent white acrylic diffusion panel for example. The diffusion panel attachments 1240 can be a slot providing a friction fit.

That is the diffusion panels 1236 can be slid into a slightly tapered slot, which comprises the diffusion panel attachments 1240. The diffusion panels 1236 are then held securely within the diffusion panel attachments 1240 allowing the photography system 1200 to be manipulated without risk of the diffusion panels 1236 becoming detached from the chassis 1202.

It has been discovered that implementing the photography system 1200 as described can provide cross lighting to teeth with a heavily diffused light. As will be appreciated this gives a glossy, yet textured look to the enamel.

That is, the light panels 1234, the diffusion panels 1236 and the imaging device 1222 coupled together as shown and described can light teeth bilaterally with significant diffusion of the light. This creates uniform, soft lighting approximating the appearance of much larger, much more expensive studio lighting.

The diffusion panel attachments 1240 together with the light panel attachments 1238 can have a fixed mounting position with respect to the imaging device 1222 and with respect to the chassis 1202. The fixed mounting position creates consistently soft light, which improves the highlights on the teeth, and significantly minimizes eye strain to the patient.

The fixed mounting of the light panels 1234 can have a fixed angle of 45 degrees off the chassis 1202, or 135 degrees spanning between the light panels 1234. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 13:
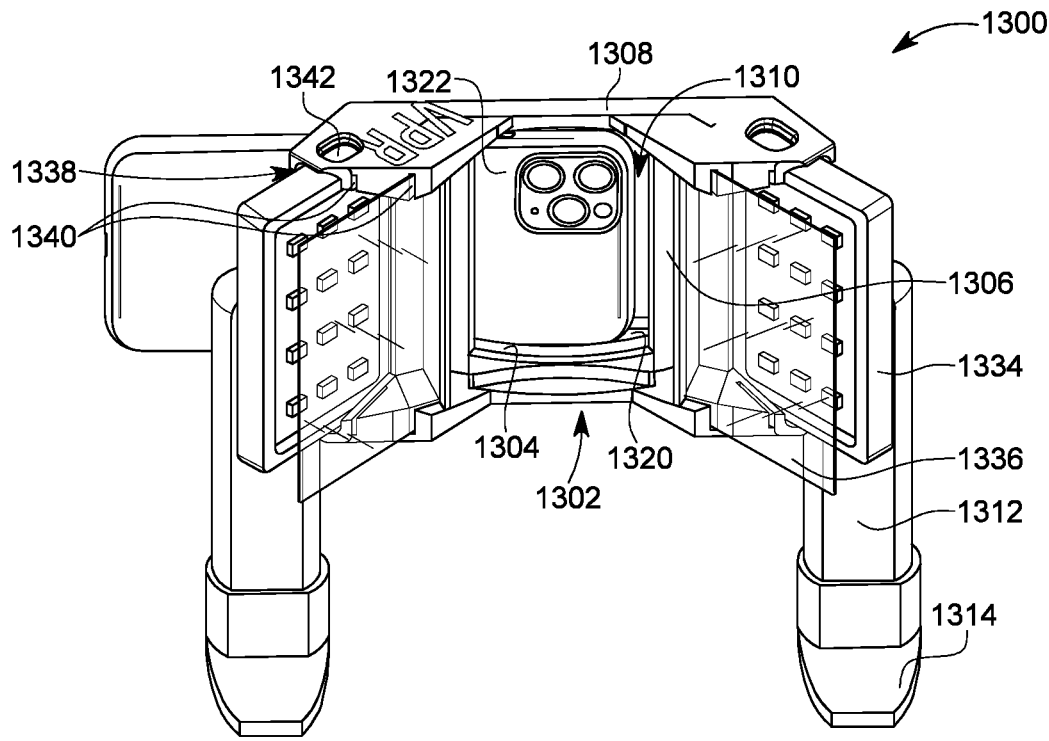
FIG. 13 is a front isometric view of the photography system in a fourth embodiment.

Referring now to FIG. 13, therein is shown a front isometric view of the photography system 1300 in a fourth embodiment. The photography system 1300 is shown having a chassis 1302. The chassis 1302 can include a chassis base 1304 spanning horizontally between two vertical chassis extensions 1306.

Figure 21:
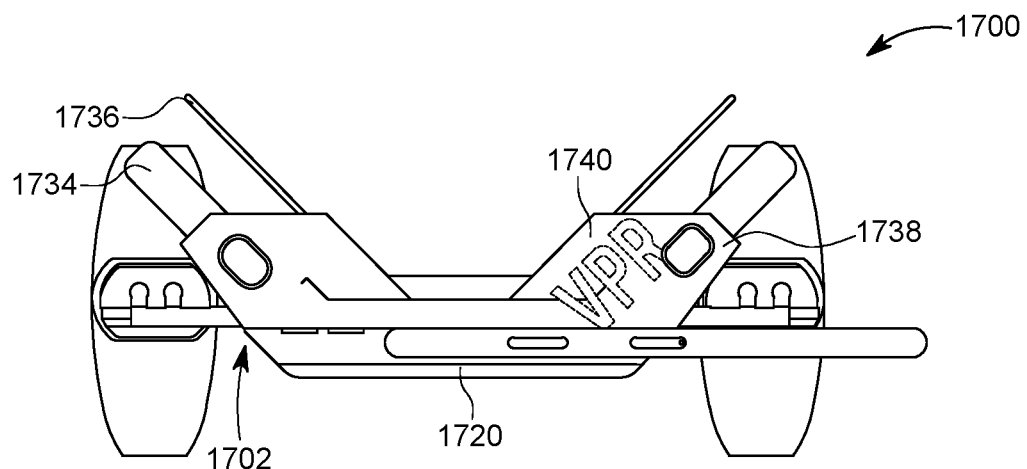
FIG. 21 is a top view of the photography system of FIG. 17.

The vertical chassis extensions 1306 can extend upward from the chassis base 1304 to a chassis top 1308. The chassis 1302 including the chassis base 1304, the vertical chassis extensions 1306 and the chassis top 1308 can form a U shape from the top, as shown in FIG. 21 for example.

The chassis 1302 including the chassis base 1304, the vertical chassis extensions 1306 and the chassis top 1308 further provide a large central aperture 1310 for stiffness and strength. The vertical chassis extensions 1306 can include chassis rails similar to the chassis rails 112 of FIG. 1 coupling handles 1312 to the vertical chassis extensions 1306.

When using the handles 1312, the shutter buttons on most phone apps are accessible with the user's right thumb. This has been discovered to provide intuitive and effective one handed operation.

The handles 1312 are depicted as both a left and right side handles coupled to either side of the chassis 1302. The left and right side handles can allow the operator to grasp the photography system 1300 while filming. Holding an imaging device with two hands stabilizes the recording of video allowing he functional movements of a patient's jaw to be documented.

The handles 1312 can be optionally coupled, with a friction fit, to feet 1314. The feet 1314 can allow the photography system 1300 to stand upright on a tabletop, which reduces the footprint, conserves counter space for other equipment, and in a clinical setting, it keeps the smartphone and the lighting elements off potentially contaminated surfaces.

It will be appreciated that the photography system 1300 can allow a user to operate the smartphone with the right hand, while positioning a mirror or retractor with the other hand. The entire rig may be inverted to use with the left hand. It is contemplated that all current smartphones will orient their apps and their images to compensate.

The chassis top 1308 can further enable the chassis 1302 to be connected to and incorporate external mounts (not shown). The external mounts can be on the vertical chassis extensions 1306 or on the chassis top 1308.

The chassis can further be fitted with a retention shelf 1320. The retention shelf 1320, together with magnets, shown in FIG. 19 for example, can secure an imaging device 1322 to the photography system 1300.

The imaging device 1322 can be a smart phone of various available widths and thicknesses. The imaging device 1322 can be positioned and affixed using the retention shelf 1320 and the magnets. The camera of the imaging device 1322 can be positioned between the vertical chassis extensions 1306 and within the central aperture 1310, for acquiring video and images.

To each of the vertical chassis extensions 1306, light panels 1334 and diffusion panels 1336 can be mounted. As is shown, one of the light panels 1334 and one of the diffusion panels 1336 are affixed to each of the vertical chassis extensions 1306.

The light panels 1334 can be affixed to the vertical chassis extensions 1306 with light panel attachments 1338 while the diffusion panels 1336 can be affixed to the vertical chassis extensions 1306 with diffusion panel attachments 1340. The light panel attachments 1338 can be an enclosed friction grip cartridge style slot.

The friction grip slot allows the light panels 1334 to be inserted until they snap or seat fully within the light panel attachments 1338. This ensures that the light panels 1334 resist forward displacement, which during use, prevent the panels from dropping towards a patient.

That is the light panels 1334 can be slid into a slightly tapered slot, which comprises the light panel attachments 1338. The light panels 1334 are then held securely within the light panel attachments 1338 allowing the photography system 1300 to be manipulated without risk of the light panels 1334 becoming detached from the chassis 1302.

The light panels 1334 can be battery powered LED panels used for illumination of dental and closeup photographs. The light panels 1334 can be rotationally oriented at 180 degrees from each other so their power switches (not pictured) are both on a single side such as on a top side.

Further, as is shown, cutouts 1342 allow access to the power and dimmer controls of the light panels 1334. The light panels 1334 can be partially enclosed to enable a cartridge style loading into the light panel attachments 1338. Cartridge style loading of the light panels 1334 allows easier insertion and removal to recharge or replace the light panels 1334.

A user may keep a second set of the light panels 1334 charged and hot swap them for continuous operation. The diffusion panels 1336 can be a translucent white acrylic diffusion panel for example. The diffusion panel attachments 1340 can be a slot providing a friction fit.

The diffusion panel attachments 1340 are shown as two slots on each of the vertical chassis extensions 1306 that allow the diffusion panels 1336 to be mounted at two different offset positions relative to the light panels 1334. One slot of the diffusion panels 1336 is mounted farther from the light panels 1334 and closer to the central aperture 1310.

The inner slots near the central aperture 1310 of the diffusion panel attachments 1340 ensures the light panels 1334, shown having discrete LEDs, are blurred into one diffused light source. Both the reflections on the surfaces of objects such as tooth enamel as well as the shadows underneath the teeth are softened. The outer slots of the diffusion panel attachments 1340, nearer the light panels 1334, allows the photography system 1300 to be more compact.

That is, the diffusion panels 1336 can be slid into a slightly tapered slot, which comprises the diffusion panel attachments 1340. The diffusion panels 1336 are then held securely within the diffusion panel attachments 1340 allowing the photography system 1300 to be manipulated without risk of the diffusion panels 1336 becoming detached from the chassis 1302.

It has been discovered that implementing the photography system 1300 as described can provide cross lighting to teeth with a heavily diffused light. As will be appreciated this gives a glossy, yet textured look to the enamel.

That is, the light panels 1334, the diffusion panels 1336 and the imaging device 1322 coupled together as shown and described can light teeth bilaterally with significant diffusion of the light. This creates uniform, soft lighting approximating the appearance of much larger, much more expensive studio lighting.

The diffusion panel attachments 1340 together with the light panel attachments 1338 can have a fixed mounting position with respect to the imaging device 1322 and with respect to the chassis 1302. The fixed mounting position creates consistently soft light, which improves the highlights on the teeth, and significantly minimizes eye strain to the patient.

The fixed mounting of the light panels 1334 can have a fixed angle of 45 degrees off the chassis 1302, or 135 degrees spanning between the light panels 1334. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 14:
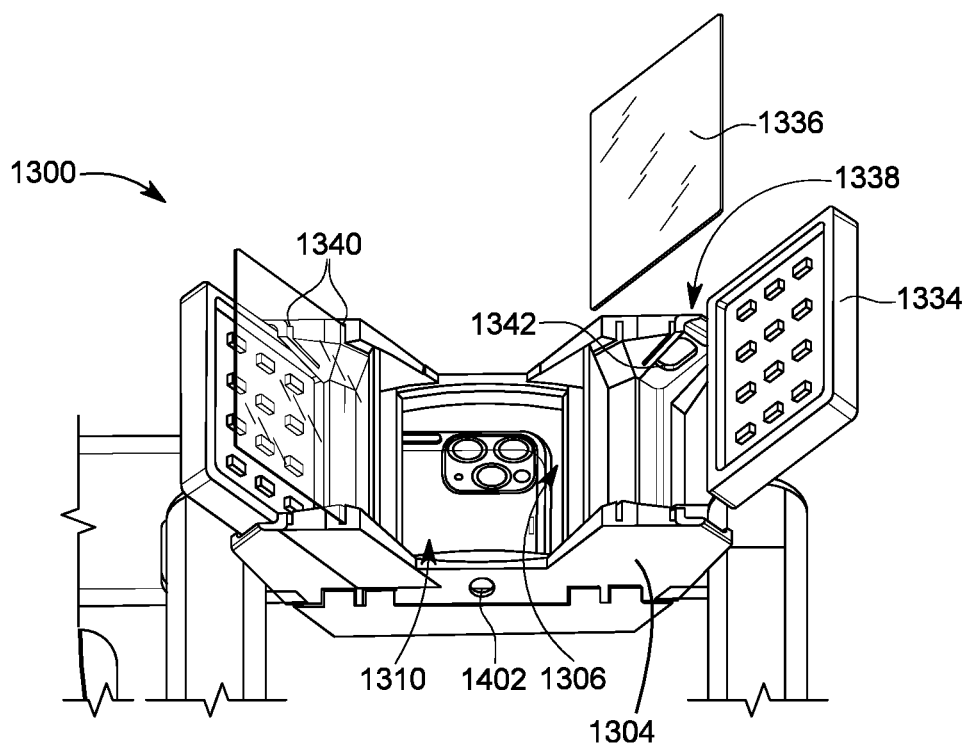
FIG. 14 is a bottom isometric view of the photography system of FIG. 13 in a light panel and diffusion panel mounting phase of operation.

Referring now to FIG. 14, therein is shown a bottom isometric view of the photography system 1300 of FIG. 13 in a light panel 1334 and diffusion panel 1336 mounting phase of operation.

The light panels 1334 are shown affixed and being affixed to the vertical chassis extensions 1306 with the light panel attachments 1338 while the diffusion panels 1336 are shown affixed and being affixed to the vertical chassis extensions 1306 with the diffusion panel attachments 1340. The light panel attachments 1338 can be an enclosed friction grip cartridge style slot.

The friction grip slot allows the light panels 1334 to be inserted until they snap or seat fully within the light panel attachments 1338. This ensures that the light panels 1334 resist forward displacement, which during use, prevent the panels from dropping towards a patient.

That is the light panels 1334 can be slid into a slightly tapered slot, which comprises the light panel attachments 1338. The light panels 1334 are then held securely within the light panel attachments 1338 allowing the photography system 1300 to be manipulated without risk of the light panels 1334 becoming detached from the light panel attachments 1338.

The light panels 1334 can be battery powered LED panels used for illumination of dental and closeup photographs. The light panels 1334 can be rotationally oriented at 180 degrees from each other so their power switches (not pictured) are both on a single side such as on a top side.

Further, as is shown, cutouts 1342 allow access to the power and dimmer controls of the light panels 1334. The light panels 1334 can be partially enclosed to enable a cartridge style loading into the light panel attachments 1338. Cartridge style loading of the light panels 1334 allows easier insertion and removal to recharge or replace the light panels 1334.

A user may keep a second set of the light panels 1334 charged and hot swap them for continuous operation. The diffusion panels 1336 can be a translucent white acrylic diffusion panel for example. The diffusion panel attachments 1340 can be a slot providing a friction fit.

The diffusion panel attachments 1340 are shown as two slots on each of the vertical chassis extensions 1306 that allow the diffusion panels 1336 to be mounted at two different offset positions relative to the light panels 1334. One slot of the diffusion panels 1336 is mounted farther from the light panels 1334 and closer to the central aperture 1310.

The inner slots near the central aperture 1310 of the diffusion panel attachments 1340 ensures the light panels 1334, shown having discrete LEDs, are blurred into one diffused light source. Both the reflections on the surfaces of objects such as tooth enamel as well as the shadows underneath the teeth are softened. The outer slots of the diffusion panel attachments 1340, nearer the light panels 1334, allows the photography system 1300 to be more compact.

That is, the diffusion panels 1336 can be slid into a slightly tapered slot, which comprises the diffusion panel attachments 1340. The diffusion panels 1336 are then held securely within the diffusion panel attachments 1340 allowing the photography system 1300 to be manipulated without risk of the diffusion panels 1336 becoming detached from the diffusion panel attachments 1340.

It has been discovered that implementing the photography system 1300 as described can provide cross lighting to teeth with a heavily diffused light. As will be appreciated this gives a glossy, yet textured look to the enamel.

That is, the light panels 1334, the diffusion panels 1336 and the imaging device 1322, of FIG. 13, coupled together as shown and described can light teeth bilaterally with significant diffusion of the light. This creates uniform, soft lighting approximating the appearance of much larger, much more expensive studio lighting.

The chassis base 1304 can further be seen to include a frame mount 1402. The frame mount 1402 can be a mount configured for compatibility with a tripod, monopod, or gimbal for more stable video quality. It is further contemplated that some users may optionally mount a pistol grip to the frame mount 1402.

Figure 15:
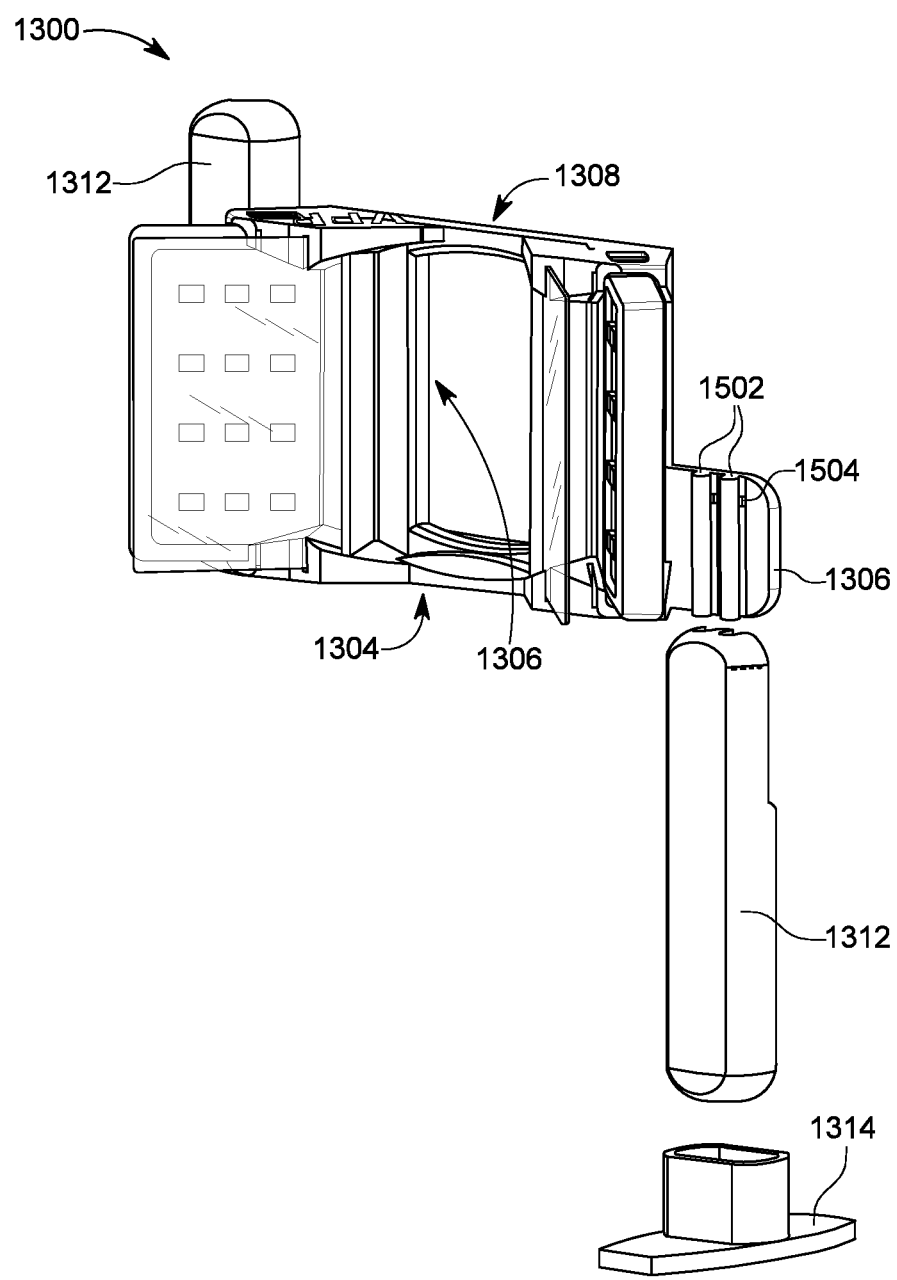
FIG. 15 is a side isometric view of the photography system of FIG. 13 in a handle mounting phase of operation.

Referring now to FIG. 15, therein is shown a side isometric view of the photography system 1300 of FIG. 13 in a handle 1312 mounting phase of operation. The vertical chassis extensions 1306 are shown to extend upward from the chassis base 1304 to the chassis top 1308. The vertical chassis extensions 1306 can include chassis rails 1502 similar to the chassis rails 112 of FIG. 1 coupling handles 1312 to the vertical chassis extensions 1306.

Illustratively for example, the chassis rails 1502 can provide a slot mechanism like a precision attachment on a partial denture. That is, male dual rails on the vertical extensions 1306 slide into corresponding dual female slots in the handles 1312. The handles 1312 can snap into place when the handles 1312 are fully seated as indicated by a seating bump 1504 formed on the chassis rails 1502.

The handles 1312 may be removed or mounted in a reverse position as shown, for example coupled to the far side of the photography system 1300. The chassis rails 1502 allow for interchangeable handles with differing form factors or functions.

The handles 1312 can be optionally shown coupled to feet 1314. The feet 1314 can allow the photography system 1300 to stand upright on a tabletop, which reduces the footprint, conserves counter space for other equipment, and in a clinical setting, it keeps the smartphone and the lighting elements off potentially contaminated surfaces.

Figure 16:
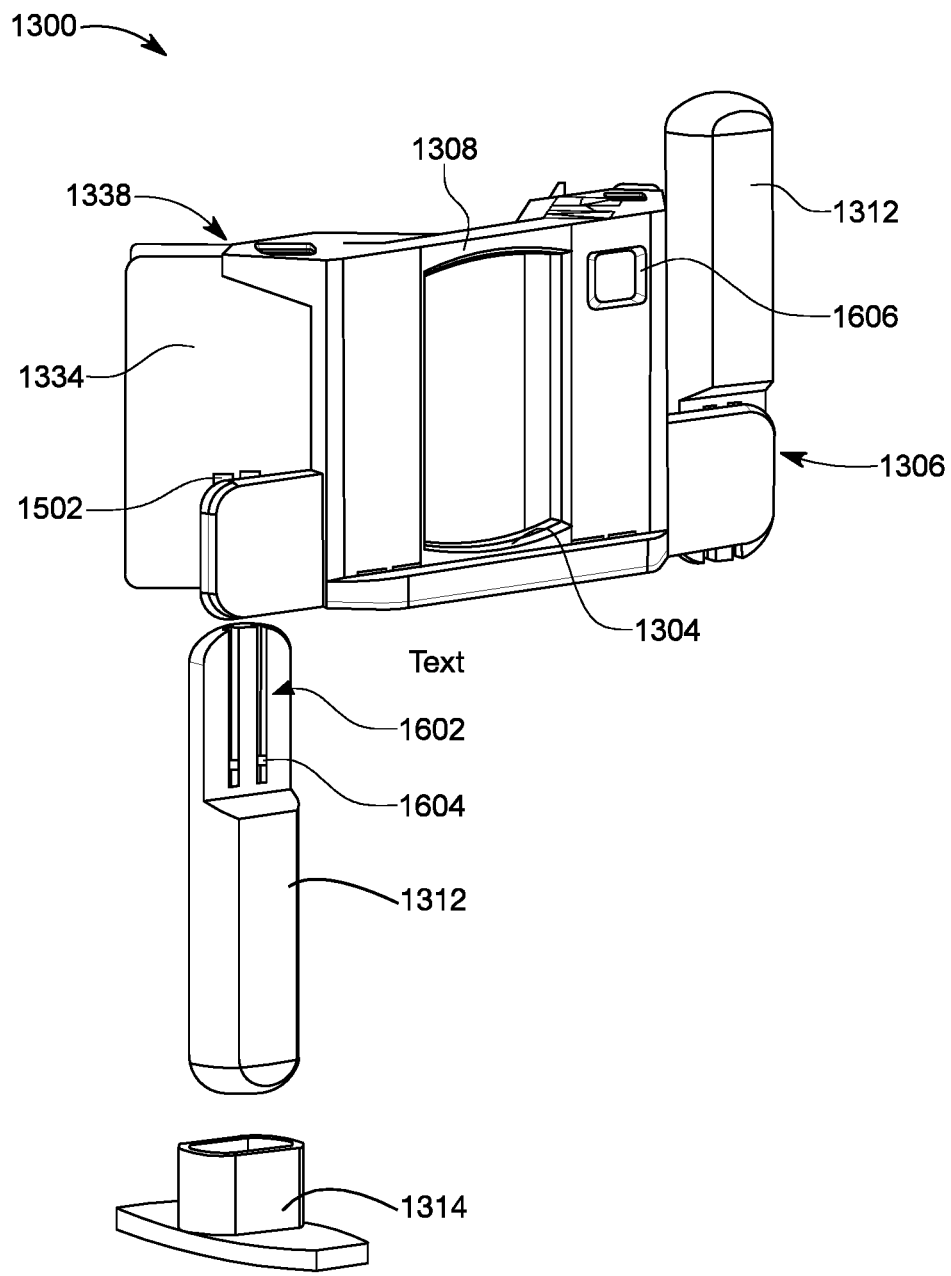
FIG. 16 is a back isometric view of the photography system of FIG. 15.

Referring now to FIG. 16, therein is shown a back isometric view of the photography system 1300 of FIG. 15. The vertical chassis extensions 1306 are shown to extend upward from the chassis base 1304 to the chassis top 1308. The vertical chassis extensions 1306 can include chassis rails 1502 similar to the chassis rails 112 of FIG. 1 coupling the handles 1312 to the vertical chassis extensions 1306.

Illustratively for example, the chassis rails 1502 can provide a slot mechanism like a precision attachment on a partial denture. That is, male dual rails on the vertical extensions 1306 slide into corresponding dual female slots 1602 in the handles 1312. The handles 1312 can snap into place when the handles 1312 are fully seated as indicated by a seating dimple 1604 formed on the dual female slots 1602.

The handles 1312 may be removed or mounted in a reverse position as shown, for example coupled to the photography system 1300 and extending from the chassis base 1304 toward the chassis top 1308. That is, the handles 1312 can be mounted to extend up from the chassis rails 1502 or down from the chassis rails 1502. The chassis rails 1502 allow for interchangeable handles with differing form factors or functions.

The handles 1312 can be optionally shown coupled to feet 1314. The feet 1314 can allow the photography system 1300 to stand upright on a tabletop, which reduces the footprint, conserves counter space for other equipment, and in a clinical setting, it keeps the smartphone and the lighting elements off potentially contaminated surfaces.

One of the vertical extensions 1306 can be seen having a pass through port 1606. Because the light panels 1334 are affixed to the vertical chassis extensions 1306 by being enclosed within the light panel attachments 1338, the pass through port 1606 provides the user access to the USB charging port of the light panels 1334. The light panels 1334 do not have to be removed in order to recharge them. The left light panel 1334 has a USB port off to the left side and therefore does not require the pass through port 1606.

Figure 17:
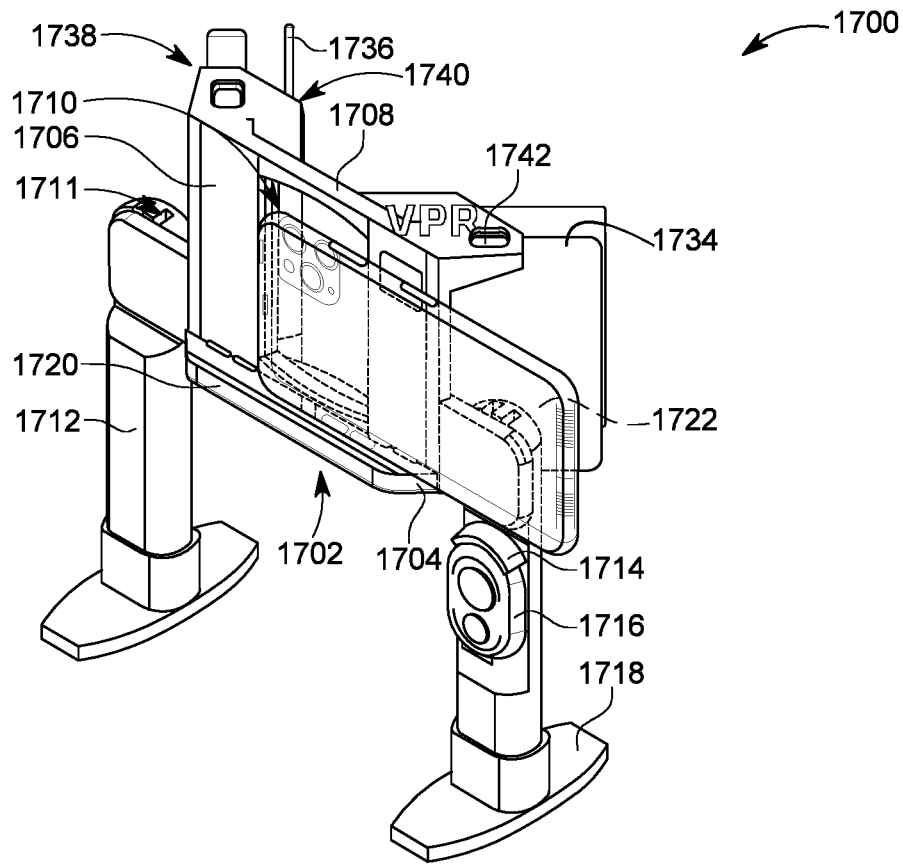
FIG. 17 is a back isometric view of the photography system in a fifth embodiment.

Referring now to FIG. 17, therein is shown a back isometric view of the photography system 1700 in a fifth embodiment. The photography system 1700 is shown having a chassis 1702. The chassis 1702 can include a chassis base 1704 spanning horizontally between two vertical chassis extensions 1706.

The vertical chassis extensions 1706 can extend upward from the chassis base 1704 to a chassis top 1708. The chassis 1702 including the chassis base 1704, the vertical chassis extensions 1706 and the chassis top 1708 can form a U shape from the top, as shown in FIG. 21 for example.

The chassis 1702, including the chassis base 1704, the vertical chassis extensions 1706 and the chassis top 1708, further provide a large central aperture 1710 with high stiffness and strength. The vertical chassis extensions 1706 can include chassis rails 1711 similar to the chassis rails 112 of FIG. 1 coupling handles 1712 to the vertical chassis extensions 1706.

Illustratively for example, the chassis rails 1711 can provide a slot mechanism like a precision attachment on a partial denture. That is, male dual rails on the vertical extensions 1706 slide into corresponding dual female slots in the handles 1712. The handles 1712 can snap into place when the handles 1712 are fully seated. The handles 1712 may be removed or mounted in a reverse position as shown, for example in FIGS. 15 and 16 for more compact storage. The new chassis rails 1711 allows for interchangeable handles with differing form factors or functions.

As is shown, one of the handles 1712 includes a trigger enclosure 1714 for securing the trigger 1716 to the handle 1712. The operator may use the trigger 1716 to capture an image or video without physical contact with the imaging device. Illustratively, for example, the trigger 1716 can be a Bluetooth remote trigger and may be removed from the handle 1712 in order to change the battery as needed. This can be accomplished with the USB charging port shown on the bottom of the trigger 1716. This alternative handle 1712, which includes the trigger enclosure 1714, can also create a longer grip which may be more comfortable for some users.

The handles 1712 are depicted as both a left and right side handles coupled to either side of the chassis 1702. The left and right side handles can allow the operator to grasp the photography system 1700 while filming. Holding an imaging device with two hands stabilizes the recording of video allowing he functional movements of a patient's jaw to be documented.

The handles 1712 can be optionally coupled, with a friction fit, to feet 1718. The feet 1718 can allow the photography system 1700 to stand upright on a tabletop, which reduces the footprint, conserves counter space for other equipment, and in a clinical setting, it keeps the smartphone and the lighting elements off potentially contaminated surfaces.

It will be appreciated that the photography system 1700 can allow a user to operate the smartphone with the right hand, while positioning a mirror or retractor with the other hand. The entire rig may be inverted to use with the left hand. It is contemplated that all current smartphones will orient their apps and their images to compensate.

The chassis top 1708 can further enable the chassis 1702 to be connected to and incorporate external mounts (not shown). The external mounts can be on the vertical chassis extensions 1706 or on the chassis top 1708.

The chassis can further be fitted with a retention shelf 1720. The retention shelf 1720, together with magnets, shown in FIG. 19 for example, can secure an imaging device 1722 to the photography system 1700.

The imaging device 1722 can be a smart phone of various available widths and thicknesses. The imaging device 1722 can be positioned and affixed using the retention shelf 1720 and the magnets. The camera of the imaging device 1722 can be positioned between the vertical chassis extensions 1706 and within the central aperture 1710, for acquiring video and images.

The trigger 1716 can be an electronic trigger that interfaces with the imaging device 1722. When paired with the imaging device 1722, the trigger 1716 will initiate the capture of a still image or video image with the imaging device 1722. The trigger 1716 can include physical button, as opposed to the touchscreen button on the imaging device 1716. Some operators may prefer the tactile sensation of a button. That makes it easier to locate without looking and also gives a positive clicking sensation when an image is taken.

To each of the vertical chassis extensions 1706, light panels 1734 and diffusion panels 1736 can be mounted. As is shown, one of the light panels 1734 is affixed to each of the vertical chassis extensions 1706.

The light panels 1734 can be affixed to the vertical chassis extensions 1706 with light panel attachments 1738 while the diffusion panels 1736 can be affixed to the vertical chassis extensions 1706 with diffusion panel attachments 1740. The light panel attachments 1738 can be an enclosed friction grip cartridge style slot.

The friction grip slot allows the light panels 1734 to be inserted until they snap or seat fully within the light panel attachments 1738. This ensures that the light panels 1734 resist forward displacement, which during use, prevent the panels from dropping towards a patient.

That is the light panels 1734 can be slid into a slightly tapered slot, which comprises the light panel attachments 1738. The light panels 1734 are then held securely within the light panel attachments 1738 allowing the photography system 1700 to be manipulated without risk of the light panels 1734 becoming detached from the chassis 1702.

The light panels 1734 can be battery powered LED panels used for illumination of dental and closeup photographs. The light panels 1734 can be rotationally oriented at 180 degrees from each other so their power switches (not pictured) are both on a single side such as on a top side.

Further, as is shown, cutouts 1742 allow access to the power and dimmer controls of the light panels 1734. The light panels 1734 can be partially enclosed to enable a cartridge style loading into the light panel attachments 1738. Cartridge style loading of the light panels 1734 allows easier insertion and removal to recharge or replace the light panels 1734.

A user may keep a second set of the light panels 1734 charged and hot swap them for continuous operation. The diffusion panels 1736 can be a translucent white acrylic diffusion panel for example. The diffusion panel attachments 1740 can be a slot providing a friction fit.

The diffusion panel attachments 1740 can be two slots on each of the vertical chassis extensions 1706 that allow the diffusion panels 1736 to be mounted at two different offset positions relative to the light panels 1734. One slot of the diffusion panels 1736 is mounted farther from the light panels 1734 and closer to the central aperture 1710.

The inner slots near the central aperture 1710 of the diffusion panel attachments 1740 ensures the light panels 1734, shown having discrete LEDs, are blurred into one diffused light source. Both the reflections on the surfaces of objects such as tooth enamel as well as the shadows underneath the teeth are softened. The outer slots of the diffusion panel attachments 1740, nearer the light panels 1734, allows the photography system 1700 to be more compact.

That is, the diffusion panels 1736 can be slid into a slightly tapered slot, which comprises the diffusion panel attachments 1740. The diffusion panels 1736 are then held securely within the diffusion panel attachments 1740 allowing the photography system 1700 to be manipulated without risk of the diffusion panels 1736 becoming detached from the chassis 1702.

It has been discovered that implementing the photography system 1700 as described can provide cross lighting to teeth with a heavily diffused light. As will be appreciated this gives a glossy, yet textured look to the enamel.

That is, the light panels 1734, the diffusion panels 1736 and the imaging device 1722 coupled together as shown and described can light teeth bilaterally with significant diffusion of the light. This creates uniform, soft lighting approximating the appearance of much larger, much more expensive studio lighting.

The diffusion panel attachments 1740 together with the light panel attachments 1738 can have a fixed mounting position with respect to the imaging device 1722 and with respect to the chassis 1702. The fixed mounting position creates consistently soft light, which improves the highlights on the teeth, and significantly minimizes eye strain to the patient.

The fixed mounting of the light panels 1734 can have a fixed angle of 45 degrees off the chassis 1702, or 135 degrees spanning between the light panels 1734. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 18:
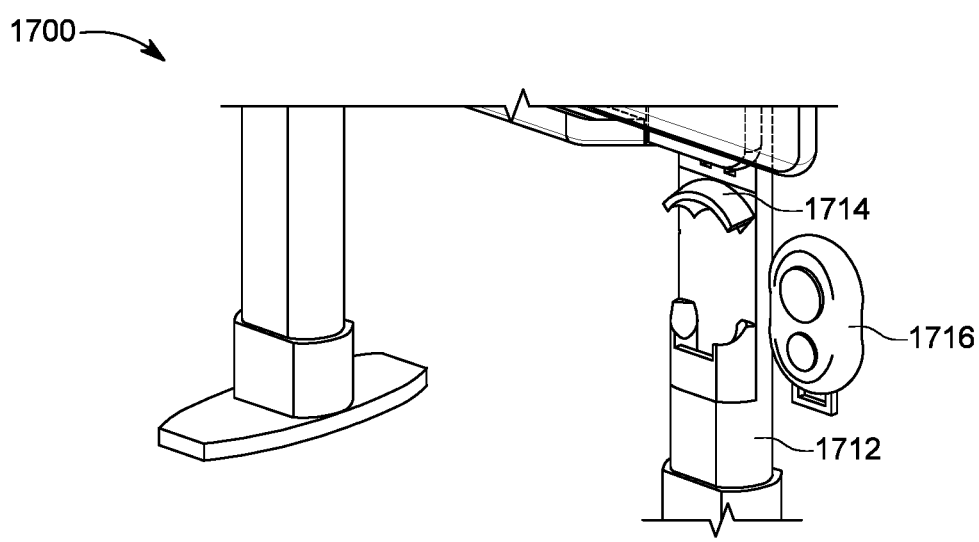
FIG. 18 is a back isometric view of the photography system of FIG. 17 in a trigger mounting phase of operation.

Referring now to FIG. 18, therein is shown a back isometric view of the photography system 1700 of FIG. 17 in a trigger 1716 mounting phase of operation. One of the handles 1712 includes the trigger enclosure 1714 for securing the trigger 1716 to the handle 1712. The operator may use the trigger 1716 to capture an image or video without physical contact with the imaging device. The trigger 1716 can be a Bluetooth remote trigger and may be removed from the handle 1712 in order to change the battery as needed. This alternative handle 1712, which includes the trigger enclosure 1714, can also create a longer grip which may be more comfortable for some users.

Figure 19:
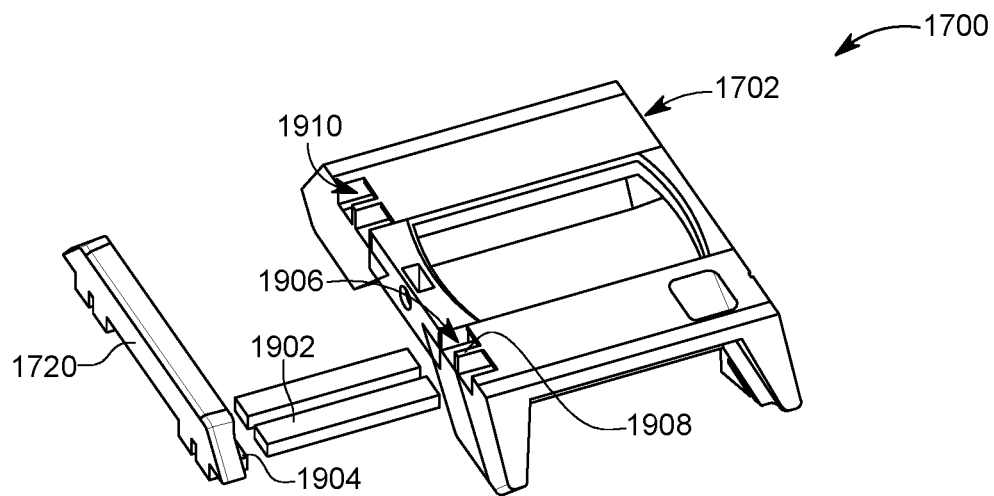
FIG. 19 is a back isometric view of the photography system of FIG. 17 in a retention shelf mounting phase of operation.

Referring now to FIG. 19, therein is shown a back isometric view of the photography system 1700 of FIG. 17 in a retention shelf 1720 mounting phase of operation.

The chassis 1702 can further be fitted with the retention shelf 1720. The retention shelf 1720, together with magnets 1902 can secure the imaging device 1722, of FIG. 17, to the photography system 1700.

The retention shelf 1720 prevents the imaging device from sliding off downwards. The retention shelf 1720 further includes sealing extensions 1904 for anchoring the retention shelf 1720 to the chassis 1702 while simultaneously seals an access opening 1906 for the magnets 1902.

The magnets 1902 can replace a screw type clamp used to retain the imaging device to the chassis 1702. The magnets 1902 can be rare earth magnets providing a strong force. A metal sticker 2002, of FIG. 20, can be applied to the back of the imaging device 1722 to anchor the imaging device 1722 to the magnets 1902.

It is contemplated that the magnets 1902 and the metal sticker 2002 should be understood as two clamping elements of a magnetic clamp. These elements could be reversed with the metal sticker being formed or affixed to the vertical extension and the magnet 1902 affixed to the imaging device 1722.

Alternatively, the two clamping elements could both be magnetic or printed magnetic stickers for ensuring a magnetic clamp between the imaging device 1722 and the vertical extension 1706. The magnetic clamp including the magnets 1902 can attract and retain the imaging device 1722 to the chassis 1702 strongly by the magnetic force placed on the metal sticker 2002.

The access openings 1906 for the magnets 1902 can further include a partition 1908. The partition 1908 can be placed between the magnets 1902. Lateral force between the two magnets 1902 compresses them against the partition 1908, preventing the magnets 1902 from sliding out or rattling within a magnet cavity 1910. The partition 1908 can be widened for strength and also to spread the surface area for magnetic retention of the smartphone.

Figure 20:
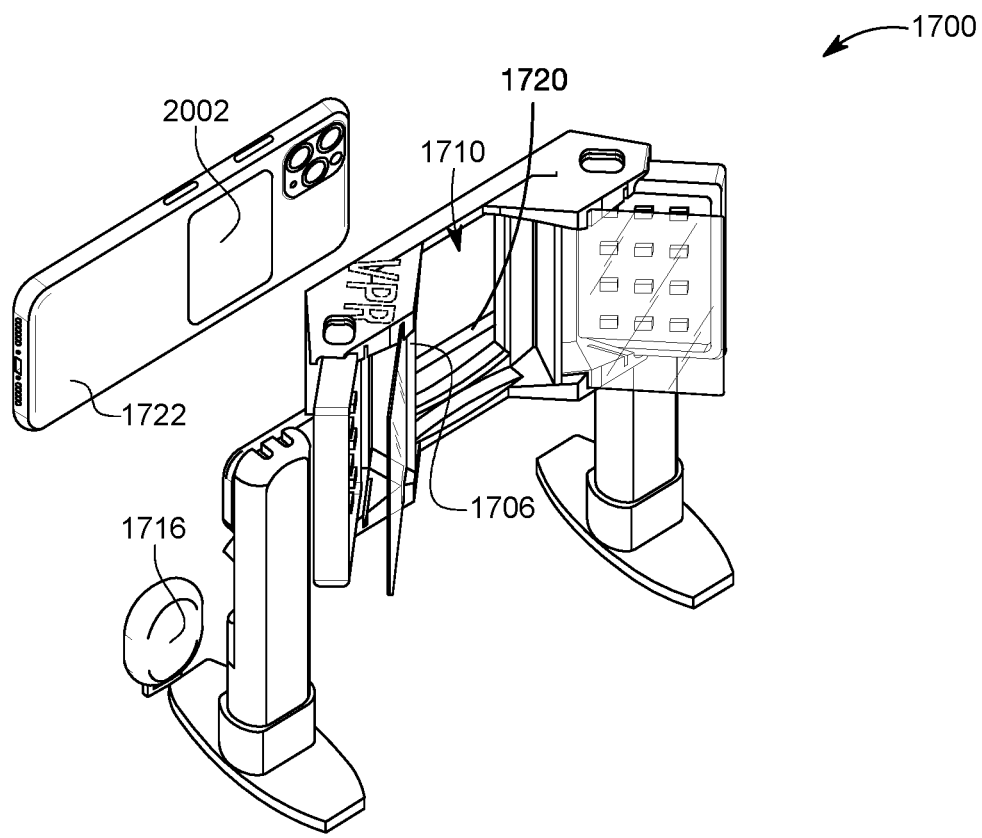
FIG. 20 is a front isometric view of the photography system of FIG. 17 in an imaging device and trigger mounting phase of operation.

Referring now to FIG. 20, therein is shown a front isometric view of the photography system 1700 of FIG. 17 in an imaging device 1722 and trigger 1716 mounting phase of operation. The imaging device 1722 is shown having a metal sticker 2002 adhered to the surface thereof.

The metal sticker 2002 must be applied to the back of the imaging device 1722. A user can then mount the imaging device 1722 simply by placing it close to the magnets 1902 of FIG. 19 contained within the vertical extension 1706. The magnets 1902 can then snap the imaging device 1722 into place against the vertical extension 1706 and the retention shelf 1720. Lateral sliding adjustments can be made to center the imaging device 1722 within the aperture 1710.

Referring now to FIG. 21, therein is shown a top view of the photography system 1700 of FIG. 17. As seen from the top, the photography system 1700 has a distinctive V shape formed by the chassis 1702 coupled to the retention shelf 1720, together with the light panel attachments 1738 holding the light panels 1734 and the diffusion panel attachments 1740 holding the diffusion panels 1736.

Figure 22:
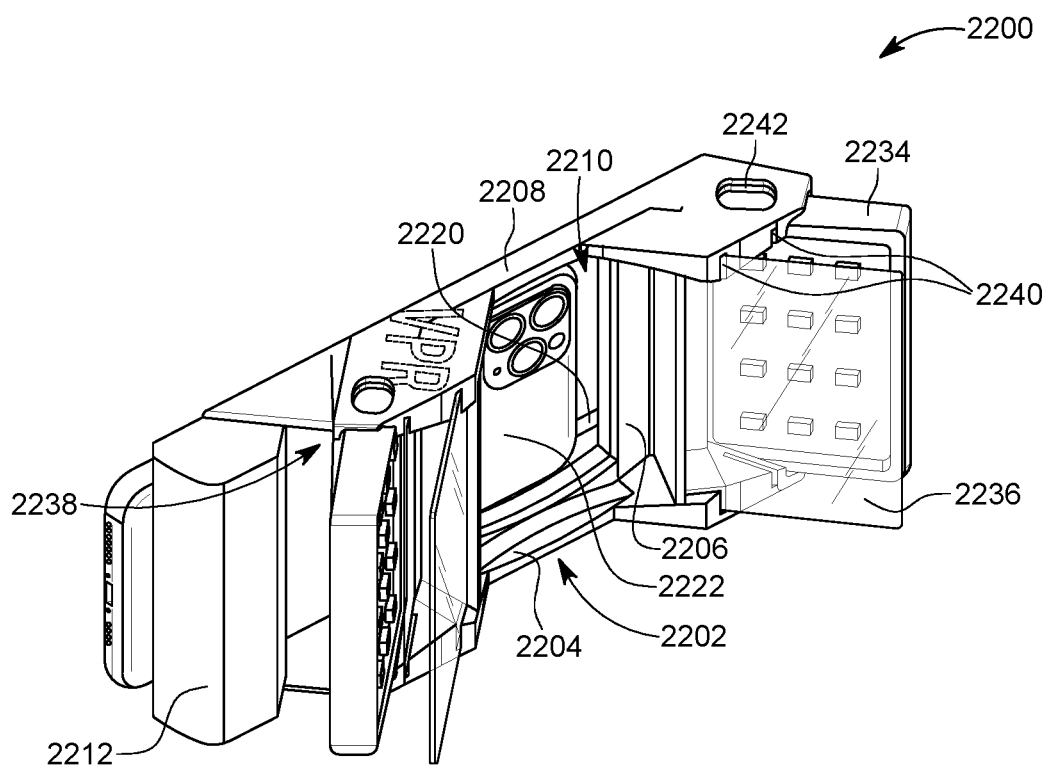
FIG. 22 is a front isometric view of the photography system in a sixth embodiment.

Referring now to FIG. 22, therein is shown a front isometric view of the photography system 2200 in a sixth embodiment. The photography system 2200 is shown having a chassis 2202. The chassis 2202 can include a chassis base 2204 spanning horizontally between two vertical chassis extensions 2206.

The vertical chassis extensions 2206 can extend upward from the chassis base 2204 to a chassis top 2208. The chassis 2202 including the chassis base 2204, the vertical chassis extensions 2206 and the chassis top 2208 can form a U shape from the top, as shown in FIG. 21 for example.

The chassis 2202, including the chassis base 2204, the vertical chassis extensions 2206 and the chassis top 2208, further provide a large central aperture 2210 with high stiffness and strength. The vertical extension 2206 can be integrally formed as a handle 2212.

The handle 2212 can be a uni-grip design in order to reduce size of the apparatus further. That is the handle 2212 can be a single grip integrated into the right (or left) side of the chassis 2202. The operator can utilize the photography system 2200 with a single hand.

It will be appreciated that the photography system 2200 can allow a user to operate the smartphone with the right hand, while positioning a mirror or retractor with the other hand. The entire rig may be inverted to use with the left hand. It is contemplated that all current smartphones will orient their apps and their images to compensate.

The chassis top 2208 can further enable the chassis 2202 to be connected to and incorporate external mounts (not shown). The external mounts can be on the vertical chassis extensions 2206 or on the chassis top 2208.

The chassis can further be fitted with a retention shelf 2220. The retention shelf 2220, together with magnets, shown in FIG. 19 for example, can secure an imaging device 2222 to the photography system 2200.

The imaging device 2222 can be a smart phone of various available widths and thicknesses. The imaging device 2222 can be positioned and affixed using the retention shelf 2220 and the magnets. The camera of the imaging device 2222 can be positioned between the vertical chassis extensions 2206 and within the central aperture 2210, for acquiring video and images.

To each of the vertical chassis extensions 2206, light panels 2234 and diffusion panels 2236 can be mounted. As is shown, one of the light panels 2234 is affixed to each of the vertical chassis extensions 2206.

The light panels 2234 can be affixed to the vertical chassis extensions 2206 with light panel attachments 2238 while the diffusion panels 2236 can be affixed to the vertical chassis extensions 2206 with diffusion panel attachments 2240. The light panel attachments 2238 can be an enclosed friction grip cartridge style slot.

The friction grip slot allows the light panels 2234 to be inserted until they snap or seat fully within the light panel attachments 2238. This ensures that the light panels 2234 resist forward displacement, which during use, prevent the panels from dropping towards a patient.

That is the light panels 2234 can be slid into a slightly tapered slot, which comprises the light panel attachments 2238. The light panels 2234 are then held securely within the light panel attachments 2238 allowing the photography system 2200 to be manipulated without risk of the light panels 2234 becoming detached from the chassis 2202.

The light panels 2234 can be battery powered LED panels used for illumination of dental and closeup photographs. The light panels 2234 can be rotationally oriented at 180 degrees from each other so their power switches (not pictured) are both on a single side such as on a top side.

Further, as is shown, cutouts 2242 allow access to the power and dimmer controls of the light panels 2234. The light panels 2234 can be partially enclosed to enable a cartridge style loading into the light panel attachments 2238. Cartridge style loading of the light panels 2234 allows easier insertion and removal to recharge or replace the light panels 2234.

A user may keep a second set of the light panels 2234 charged and hot swap them for continuous operation. The diffusion panels 2236 can be a translucent white acrylic diffusion panel for example. The diffusion panel attachments 2240 can be a slot providing a friction fit.

The diffusion panel attachments 2240 can be two slots on each of the vertical chassis extensions 2206 that allow the diffusion panels 2236 to be mounted at two different offset positions relative to the light panels 2234. One slot of the diffusion panels 2236 is mounted farther from the light panels 2234 and closer to the central aperture 2210.

The inner slots near the central aperture 2210 of the diffusion panel attachments 2240 ensures the light panels 2234, shown having discrete LEDs, are blurred into one diffused light source. Both the reflections on the surfaces of objects such as tooth enamel as well as the shadows underneath the teeth are softened. The outer slots of the diffusion panel attachments 2240, nearer the light panels 2234, allows the photography system 2200 to be more compact.

That is, the diffusion panels 2236 can be slid into a slightly tapered slot, which comprises the diffusion panel attachments 2240. The diffusion panels 2236 are then held securely within the diffusion panel attachments 2240 allowing the photography system 2200 to be manipulated without risk of the diffusion panels 2236 becoming detached from the chassis 2202.

It has been discovered that implementing the photography system 2200 as described can provide cross lighting to teeth with a heavily diffused light. As will be appreciated this gives a glossy, yet textured look to the enamel.

That is, the light panels 2234, the diffusion panels 2236 and the imaging device 2222 coupled together as shown and described can light teeth bilaterally with significant diffusion of the light. This creates uniform, soft lighting approximating the appearance of much larger, much more expensive studio lighting.

The diffusion panel attachments 2240 together with the light panel attachments 2238 can have a fixed mounting position with respect to the imaging device 2222 and with respect to the chassis 2202. The fixed mounting position creates consistently soft light, which improves the highlights on the teeth, and significantly minimizes eye strain to the patient.

The fixed mounting of the light panels 2234 can have a fixed angle of 45 degrees off the chassis 2202, or 135 degrees spanning between the light panels 2234. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 23:
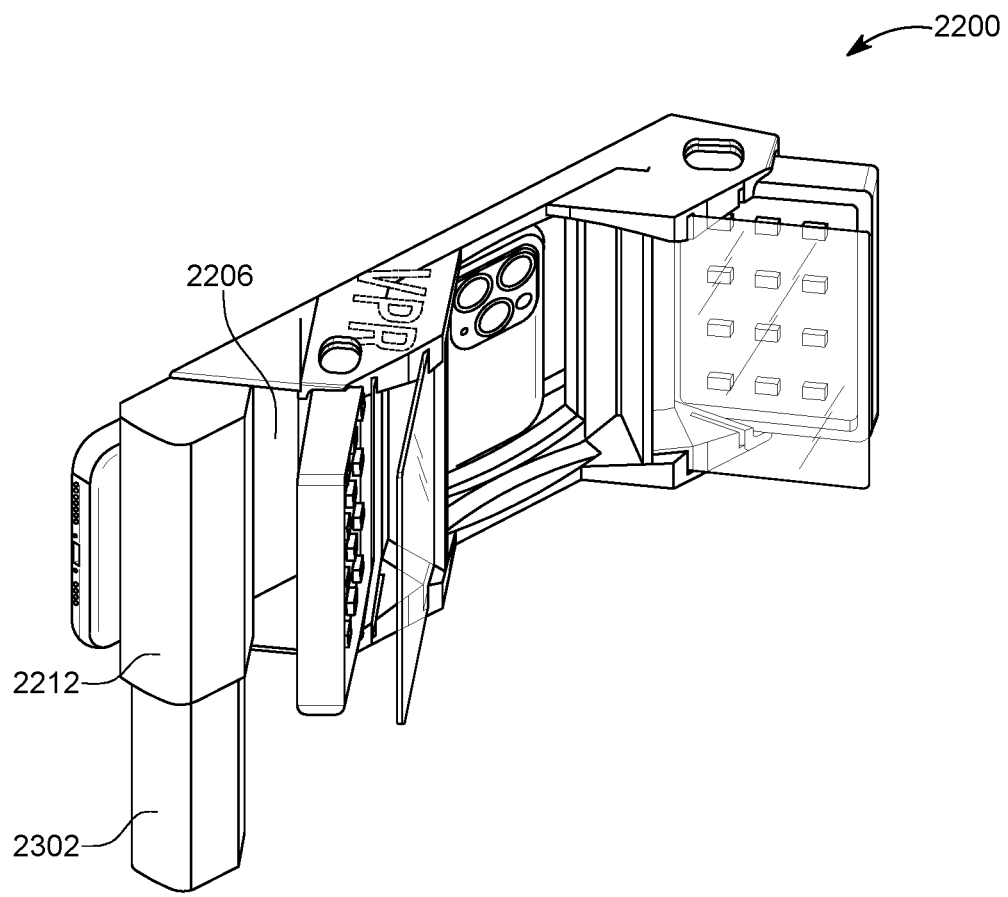
FIG. 23 is a front isometric view of the photography system of FIG. 22 in an extension phase of operation.

Referring now to FIG. 23, therein is shown a front isometric view of the photography system 2200 of FIG. 22 in an extension phase of operation. The handle 2212 formed integrally with the vertical extension 2206 is depicted having a handle extension 2302 extended from the bottom of the handle 2212 in order to provide a lower grasping point. It has been discovered that the handle extension 2302 can allow the thumb to more comfortably rest on the shutter release icon in most camera apps.

Figure 24:
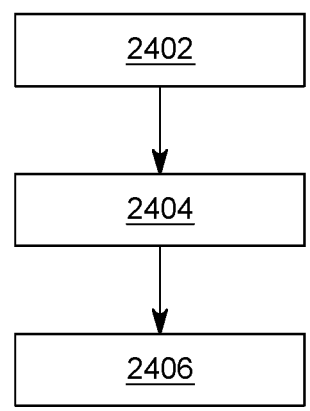
FIG. 24 is a flow chart for manufacturing the oral photography system.

Referring now to FIG. 24, therein is shown a flow chart for manufacturing the oral photography system. The method includes: providing a chassis, the chassis including a chassis base and a vertical chassis extension, the vertical chassis extension extending upward from the chassis base, and the vertical chassis extension including: a magnetic clamp having a first clamping element for securing an imaging device to the vertical chassis extension, the imaging device including a second clamping element, a diffusion panel attachment coupled to the vertical chassis extension, and a light panel attachment coupled to the vertical chassis extension in a block 2402; attaching a diffusion panel releasably affixed to the diffusion panel attachment in a block 2404; and attaching a light panel releasably affixed to the light panel attachment in a block 2406.

Thus, it has been discovered that the photography system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the photography system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. An oral photography system comprising:
a chassis, the chassis including a chassis base and a vertical chassis extension, the vertical chassis extension extending upward from the chassis base, and the vertical chassis extension including:
a magnetic clamp having a first clamping element for securing an imaging device to the vertical chassis extension, the imaging device including a second clamping element,
a diffusion panel attachment coupled to the vertical chassis extension, and
a light panel attachment coupled to the vertical chassis extension;
a diffusion panel releasably affixed to the diffusion panel attachment; and
a light panel releasably affixed to the light panel attachment.

2. The system of claim 1 wherein the vertical chassis extension includes a chassis rail coupling a handle to the vertical chassis extension.

3. The system of claim 2 wherein the handle extends up from the chassis rail or down from the chassis rail.

4. The system of claim 2 further comprising a foot coupled to the handle.

5. The system of claim 2 wherein the handle includes a trigger enclosure securing a trigger to the handle.

6. An oral photography system comprising:
a chassis, the chassis including a chassis base and vertical chassis extensions, the vertical chassis extensions extending upward from the chassis base, the chassis base spanning horizontally between the vertical chassis extensions, and one of the vertical chassis extensions including:
a magnetic clamp having a first clamping element for securing an imaging device at least partially between the vertical chassis extensions, and the imaging device including a second clamping element,
a diffusion panel attachment coupled thereto, and
a light panel attachment coupled thereto;
a diffusion panel releasably affixed to the diffusion panel attachment; and
a light panel releasably affixed to the light panel attachment.

7. The system of claim 6 wherein the light panel attachment includes a cutout allowing access to a control of the light panel.

8. The system of claim 6 further comprising a handle coupled to the chassis, the handle including a handle extension extendable from the handle.

9. The system of claim 6 further comprising a retention shelf coupled to the chassis to secure the imaging device.

10. The system of claim 6 wherein the diffusion panel attachment includes slots providing different positions for mounting the diffusion panel.

11. A method of manufacturing an oral photography system comprising:
   providing a chassis, the chassis including a chassis base and a vertical chassis extension, the vertical chassis extension extending upward from the chassis base, and the vertical chassis extension including:
      a magnetic clamp having a first clamping element for securing an imaging device to the vertical chassis extension, the imaging device including a second clamping element,
      a diffusion panel attachment coupled to the vertical chassis extension, and
      a light panel attachment coupled to the vertical chassis extension;
   attaching a diffusion panel releasably affixed to the diffusion panel attachment; and
   attaching a light panel releasably affixed to the light panel attachment.

12. The method of claim 11 further comprising coupling a handle to the vertical chassis extension with a chassis rail.

13. The method of claim 12 wherein coupling the handle coupling the handle to extend up from the chassis rail or extend down from the chassis rail.

14. The method of claim 12 further comprising coupling a foot to the handle.

15. The method of claim 12 wherein coupling the handle includes coupling the handle having a trigger enclosure securing a trigger to the handle.

16. The method of claim 11 wherein providing the chassis includes providing the chassis with the vertical chassis extension being one of two vertical chassis extensions, the vertical chassis extensions extending upward from the chassis base, and the chassis base spanning horizontally between the vertical chassis extensions.

17. The method of claim 16 wherein providing the chassis having the light panel attachment includes the light panel attachment having a cutout allowing access to a control of the light panel.

18. The method of claim 16 further comprising coupling a handle to the chassis, the handle including a handle extension extendable from the handle.

19. The method of claim 16 further comprising coupling a retention shelf to the chassis to secure the imaging device.

20. The method of claim 16 wherein providing the chassis having the diffusion panel attachment includes the diffusion panel attachment having slots providing different positions for mounting the diffusion panel.

* * * * *